(12) United States Patent
Colston, Jr. et al.

(10) Patent No.: US 9,434,997 B2
(45) Date of Patent: Sep. 6, 2016

(54) METHODS, COMPOUNDS AND SYSTEMS FOR DETECTING A MICROORGANISM IN A SAMPLE

(75) Inventors: Bill W. Colston, Jr., San Ramon, CA (US); J. Patrick Fitch, Middletown, MD (US); Shea N. Gardner, Oakland, CA (US); Peter L. Williams, San Anselmo, CA (US); Mark C. Wagner, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1322 days.

(21) Appl. No.: 12/196,238

(22) Filed: Aug. 21, 2008

(65) Prior Publication Data

US 2009/0081675 A1 Mar. 26, 2009

Related U.S. Application Data

(60) Provisional application No. 60/966,047, filed on Aug. 24, 2007.

(51) Int. Cl.
*C12Q 1/68* (2006.01)
*C12Q 1/70* (2006.01)

(52) U.S. Cl.
CPC .............. *C12Q 1/689* (2013.01); *C12Q 1/701* (2013.01)

(58) Field of Classification Search
None
See application file for complete search history.

(56) References Cited

FOREIGN PATENT DOCUMENTS

WO         02/099130         12/2002

OTHER PUBLICATIONS

Gardner et al. (J. of Clin. Micro, 2003, 41(6):2417-2427).*
Sen (J. Clin. Micro, 2000, 38(5):1953-1958).*
Ho et al. (J Clin Micro, 1991, 29(11):2543-2549).*
Colson et al. (BMC Microbiology, 2006, 6:21, 1-8).*
Johnson etal. (Infect. Immun,2000,68(3):1587-1599).*
Irina Afonina et al., "Primers with 5' flaps improve real-time PCR", BioTechniques, vol. 43, No. 6, 2007, pp. 770-774.
Stephen F. Altschul et al., "Gapped BLAST and PSI BLAST: a new generation of protein database search programs", Nucleic Acids Research, 1997, vol. 25, No. 17 3389-3402.
Jannine Brownie et al., "The elimination of primer-dimer accumulation in PCR", Nucleic Acids Research, 1997, vol. 25, No. 16, pp. 3235-3241.
Anna Casabianca et al, "Fast and sensitive quantitative detection of HIV DNA in whole blood leucocytes by SYBR green I real-time PCR assay", Molecular and Cellular Probes 21 (2007) 368-378.
Ramu Chenna et al., "Multiple sequence alignment with the Clustal series of programs", Nucleic Acids Research, 2003, vol. 31, No. 13,pp. 3497-3500.

Todd Z. DeSantis et al., "High-Density Universal 16S rRNA Microarray Analysis Reveals Broader Diversity than Typical Clone Library When Sampling the Environment", Microbial Ecology vol. 53, 371-383 (2007).
David J. Ecker et al., "The Ibis TSOOO Universal Biosensor: An Automated Platform for Pathogen Identification and Strain Typing", JALA Dec. 2006 11:341-351.
Sean R. Eddy, "Profile hidden Markov models", Bioinformatics, vol. 14 No. 9 1998, pp. 755-763.
Robert C. Edgar, "MUSCLE: multiple sequence alignment with high accuracy and high throughput", Nucleic Acids Research, 2004 vol. 32 No. 5, 1792-1797.
Robert A. Edwards et al., "Viral metagenomics", Nature Reviews Microbiology, 3:504-510, 2005.
S. Escutenaire et al., "SYBR Green real-time reverse transcription-polymerase chain reaction assay for the generic detection of coronaviruses", Archives of Virology, (2007) 152: 41-58.
Michael D. Gadberry et al., "Primaclade-a flexible tool to find conserved PCR primers across multiple species", Bioinformatics, vol. 21 No. 7, 2005, pp. 1263-1264.
Shea N. Gardner et al., "Limitations of TaqMan PCR for Detecting Divergent Viral Pathogens Illustrated by Hepatitis A, B, C, and E Viruses and Human Immunodeficiency Virus", Journal of Clinical Microbiology, Jun. 2003, p. 2417-2427, vol. 41, No. 6.
Yu-Cheng Huang et al., "Integrated minimum-set primers and unique probe design algorithms for differential detection on symptom-related pathogens", Bioinformatics, vol. 21 No. 24, 2005, pp. 4330-4337.
Omar J. Jabado et al., "Greene SCPrimer: a rapid comprehensive tool for designing degenerate primers from multiple sequence alignments", Nucleic Acids Research, 2006, vol. 34, No. 22 6605-6611.
Simon N. Jarman, "Amplicon: software for designing PCR primers on aligned DNA sequences" Bioinformatics, vol. 20 No. 10, 2004, pp. 1644-1645.
Amy Kistler et al., "Pan-Viral Screening of Respiratory Tract Infections in Adults With and Without Asthma Reveals Unexpected Human Coronavirus and Human Rhinovirus Diversity", JID 2007:196 (Sep. 15).
Daryl Lamson et al., "MassTag Polymerase-Chain-Reaction Detection of Respiratory Pathogens, Including a New Rhinovirus Genotype, That Caused Influenza-Like Illness in New York State during 2004-2005", pp. 1398-1402 JID 2006:194 (Nov. 15).
Baochuan Lin et al., Broad-spectrum respiratory tract pathogen identification using resequencing DNA Inicroarrays, Genome Research, 16:527-535, 2006.

(Continued)

*Primary Examiner* — Stephanie K Mummert
(74) *Attorney, Agent, or Firm* — Steinfl & Bruno, LLP

(57) ABSTRACT

Methods to identify a set of probe polynucleotides suitable for detecting a set of targets and in particular methods for identification of primers suitable for detection of target microorganisms related polynucleotides, set of polynucleotides and compositions, and related methods and systems for detection and/or identification of microorganisms in a sample.

10 Claims, 19 Drawing Sheets

(56) References Cited

OTHER PUBLICATIONS

Baochuan Lin et al, "Using a Resequencing Microarray as a Multiple Respiratory Pathogen Detection Assay", Journal of Clinical Microbiology, Feb. 2007, p. 443-452, vol. 45, No. 2.

Chaim Linhart et al., "The degenerate primer design problem", Bioinformatics, vol. 18 Suppl. 1, 2002, pp. 5172-5180.

J.S. Mackenzie et al., Emerging Viral Diseases of Southeast Asia and the Western Pacific, Emerging Infectious Diseases, vol. 7, No. 3 Supplement, Jun. 2001.

Marcel Margulies et al., "Genome sequencing in microfabricated high-density picolitre reactors", Nature, vol. 437,:376-380, 2005.

Nicholas R. Markham et al., "DINAMelt web server for nucleic acid melting prediction", Nucleic Acids Research, 2005. vol. 33, Web Server issue W577-W581.

Santosh Nanda et al., "Universal virus detection by degenerate-oligonucleotide primed polymerase chain reaction of purified viral nucleic acids", Journal of Virological Methods 152 (2008) 18-24.

Gustavo Palacios et al., "Panmicrobial Oligonucleotide Array for Diagnosis of Infectious Diseases", Emerging Infectious Diseases, vol. 13, No. 1, pp. 73-81, Jan. 2007.

Jean-Philippe Pichon et al., "Quantitative multiplex degenerate PCR for human endogenous retrovirus expression profiling", Nature Protocols, vol. I No. 6, 2006, pp. 2831-2838.

Adrian E. H. Png et al., "Primer design for whole genome amplification using genetic algorithms", In Silico Biology 6, (2006) pp. 1-10.

Phenix-Lan Quan et al, "Detection of Respiratory Viruses and Subtype Identification of Influenza A Viruses by GreeneChipResp Oligonucleotide Microarray", Journal of Clinical Microbiology, Aug. 2007, p. 2359-2364, vol. 45, No. 8.

John Rachlin et al., "MuPlex: multi-objective multiplex PCR assay design", W544-W547 Nucleic Acids Research, 2005. vol. 33, Web Server issue.

Rangarajan Sampath et al., "Rapid Identification of Emerging Infectious Agents Using PCR and Electrospray Ionization Mass Spectrometry", Ann. N. Y. Acad. Sci. 1102: 109-120 (2007). Abstract.

Timothy M. Rose et al., "CODEHOP (COnsensus-DEgenerate Hybrid Oligonucleotide Primer) PCR primer design," Nucleic Acids Research, 2003, vol. 31, No. 13 3763-3766.

Anthony P. Shuber et al., "A Simplified Procedure for Developing Multiplex PCRs", Genome Research 5:488-493, 1995.

Xin-Wei Wang et al., "Development and application of an oligonucleotide microarray for the detection of food-borne bacterial pathogens", Appl Microbiol Biotechnol (2007) 76:225-233.

David Wang et al., "Microarray-based detection and genotyping of viral pathogens", PNAS , Nov. 26, 2002, vol. 99, No. 24, pp. 15687-15692.

David Wang et al., "Viral Discovery and Sequence Recovery Using DNA Microarrays", PLoS Biology, 2003, vol. 1, Issue 2, p. 257-260.

Mark E. J. Woolhouse, "Where Do Emerging Pathogens Come from?", Nov. 2006 Microbe 1:511-515.

Tania M. Wetzel et al., "Real-Time PCR Assay for Detection and Quantification of Hepatitis B Virus Genotypes A to G", Journal of Clinical Microbiology, Sep. 2006, p. 3325-3333, vol. 44, No. 9.

\* cited by examiner

Amplicon sequence virus_num 0:

virus name: >gi|37223495|gb|AY390432.1| Foot-and-mouth disease virus Asia1 strain YNBS/58, complete genome amplicon_len: 103  FP: TTCAGGCATAGAAGCTT (revcomp of AAGCTTCTATGCCTGAA)  RP: AGGATGCCCTTCAGGTA  Start: 931  End: 1033
AGGATGCCCTTCAGGTACCCCGAGGTAACATCTGACACTCGGATCTGAGGGGACTGGGACTTCTTTAAAAGTGCCCGGTTTAA
AAAGCTTCTATGCCTGAA
amplicon_len: 149  FP: CGCAGGTAAAGTGATCT (revcomp of AGATCACTTTACCTGCG)  RP: CTCTCCTTTGCACGCCG  Start: 7870  End: 8018
CTCTCCTTTGCACGCCGTGGGACCATACAGGAGAAGTTGATCTCCGTGGCAGGACTCGCCGTCCACTCTCGACCTGACGAGTAC
CGGCGTCTCTTCGAGCCCTTCCAGGGCCTCTTTGAGATTCCAAGCTACAGATCACTTTACCTGCG
amplicon_len: 361  FP: CACGTACTTTCTCCATCG (revcomp of CGATGGAGAAAGTACGTG)  RP: GTCATCTTCTCCAAACAC  Start: 6799  End: 7159
GTCATCTTCTCCAAACACAAAGGGGACACAAAGATGACCGAGGAGGACAAAGCGCTGTTCCGCCGCTGCGCTGCTGACTACGCG
TCACGATTGCACAGGGTACTCGGTACGGCAAATGCCCCACTGAGCATCTACGAGGCAATCAAAGGCGTCGACGGTCTTGACGCC
ATGGAGCCAGATACTGCGCCTGGTCTCCCCTGGGCCC
TCCAGGGGAAGCGCCGCGGCGCACTGATTGACTTCGAGAACGGCACGGTCGGACCCGAGGTCGCGGCTGCCCTAGAGCTCATG
GAGAAAGAGAAATACAAATTTGTTTGTCAGACCTTCCTGAAGGACGAGATTCGCCCGATGGAGAAAGTACGTG
...and so on for each sequence

Amplicon distribution
mean number bands: 2
min number bands: 1
max number bands: 3 amp string: 103_149_361  (i.e. bands of length 103, 149, and 361 are predicted)
ID: >gi|37223495|gb|AY390432.1| Foot-and-mouth disease virus Asia1 strain YNBS/58, complete genome amp string: 104_149
ID: >gb|AY593755.1|gi|48610766|Foot-and-mouth disease virus A isolate a15thailand iso43, complete genome ID: >gb|AY593830.1|gi|48610916|Foot-and-mouth disease virus C isolate c7poland iso49, complete genome amp string: 104_149_361
ID: >emb|AJ320488.1|gi|18074006|Foot-and-mouth disease virus O genomic RNA, isolate O1Campos, complete genome ID: >gb|AY593837.1|gi|48610930|Foot-and-mouth disease virus O isolate ouruguay-51 iso54, complete genome
...and so on for each fragment banding pattern

METHODS, COMPOUNDS AND SYSTEMS FOR DETECTING A MICROORGANISM IN A SAMPLE

CROSS REFERENCE TO RELATED APPLICATIONS

This application claims priority to U.S. Provisional Application entitled "Method for Developing Unique Genetic Signatures for Viral Characterization" Ser. No. 60/966,047, filed on Aug. 24, 2007, the disclosure of which is incorporated herein by reference in its entirety.

STATEMENT OF GOVERNMENT GRANT

The United States Government has rights in this invention pursuant to Contract No. DE-AC52-07NA27344 between the U.S. Department of Energy and Lawrence Livermore National Security, LLC, for the operation of Lawrence Livermore National Security.

TECHNICAL FIELD

The present disclosure relates to detection and/or identification of polynucleotides sequences and of targets associated thereto, especially microorganisms, and in particular of viruses and bacteria.

BACKGROUND

High sensitivity detection of microorganisms and in particular of viruses has been a challenge in the field of biological molecule analysis, in particular when aimed at detection of a plurality of microorganisms. Whether for pathological examination or for fundamental biology studies, several methods are commonly used for the detection of various classes of microorganisms.

In particular, researchers employ numerous approaches for viral detection and discovery, including metagenomic sequencing [ref. 5], microarrays [ref. 9, 10, 12, 13, 18, 21, 24 and 25], or multiplex degenerate PCR followed by other methods of characterization such as mass spectrometry [ref. 4, 11, 22] or amplicon sequencing [ref. 8].

PCR is a rapid and cost effective technique suitable for the purpose. In some applications, however, PCR relies on specific primer sets, and it does not scale well for detection of many diverse targets, and in particular of many diverse microorganisms.

In case of viruses, high levels of diversity and lack of any universally conserved nucleotide or amino acid sequence regions makes it a challenge to detect well-characterized viruses and extremely difficult to discover novel viruses by methods that involve sequence-specific amplification. In contrast, bacteria contain universally conserved 16s rRNA sequences from which conserved primers may be designed, allowing amplification of rRNA coding regions from novel, unsequenced bacteria. [ref. 3, 26] Bacterial rRNA sequences vary sufficiently for discrimination to the family, genus, and sometimes even the species level.

As a consequence, primer design for detection and/or identification of known or unknown microorganisms, especially viruses, can be challenging. Nevertheless, PCR-based techniques for viral amplification and identification are common at the species or strain level. [ref. 6, 7, 19, 27]. These rely on careful primer design from the most conserved regions available, taking advantage of degenerate primers and/or replacement of variable positions with inosine bases, and the design and multiplex optimization of minimal sets of signatures which must be used in combination to ensure detection of all known variants.

However, multiplex primer design for many highly divergent targets is challenging, since usually no universally conserved primers exist to amplify fragments from all targets, and finding sets of primers likely to function well in multiplex, adds to the complexity of finding conserved primer candidates.

Furthermore, currently available multiplex/degenerate primer prediction tools require multiple sequence alignment [ref. 34, 36-38, 41]. Multiple sequence alignments are often difficult to construct for many sequences, exhausting either memory or available time, or both, before an alignment is completed. Moreover, even if an alignment does complete, for some divergent target sets such as RNA virus genomes of a single species or gene homologues across species, in some cases, alignments may be of suboptimal quality, or there is so little nucleotide sequence conservation that multiple primers, possibly with degenerate positions, are required to amplify all targets.

In particular, for many organisms there are few or no conserved regions of sufficient size across all strains of a species for a pair of traditional-length primers (at least 18 bases), particularly in important single-stranded RNA viruses including influenza A, HIV1, ebola, and foot and mouth disease viruses. PCR-based specific (non-random) amplification across all viral families using typical 18+ base primers would require many thousands of PCR primers to span known viral sequence diversity.

Additionally, with PCR-based specific amplification approaches, which require specific primers for each species or strain, discovery or detection of unanticipated species is usually unlikely.

SUMMARY

Provided herein, are probe polynucleotides, and in particular primers, that are suitable for detecting a plurality of microorganisms and/or identifying unknown microorganisms and related compositions, methods and systems.

In particular, according to a first aspect, a method to identify a set of probe polynucleotides, in particular primers, suitable for detecting a set of targets, in particular, target microorganisms is disclosed. The method comprises: identifying the set of target microorganisms; and identifying a set of rules to be satisfied by target sequences. The method further comprises: identifying a set of target polynucleotides by selecting one or more target polynucleotides, so that each target polynucleotide is comprised in at least one microorganism of the target microorganisms, and each target polynucleotide comprises a target sequence satisfying to the set of rules. The method also comprises: identifying the set of probe polynucleotides by reverse complementing one or more of the target sequences of the target polynucleotides of the identified set of target polynucleotides.

According to a second aspect, a method for identification of primers suitable for detection of targets and in particular target microorganisms is disclosed. The method comprises the steps of: i) identifying a first set of candidate oligonucleotides present in at least one of the target microorganisms; ii) sorting the candidate oligonucleotides of the first set by number of target microorganisms in which they occur, and iii) identifying second and third sets of candidate oligonucleotides, said second and third sets comprising oligonucleotides lying within a distance range of the oligonucleotides of the first set of candidate oligonucleotides, the second set comprising oligonucleotides lying upstream of the first set, and the third set comprising oligonucleotides lying downstream of the first set. The method also comprises: iv) sorting the candidate oligonucleotides of the second and third sets by number of target microorganisms in which they occur; and v) selecting a most frequently occurring oligonucleotide from the first set as one primer and a most frequently occurring oligonucleotide from the second and third sets as another primer. The method still further comprises: vi) if the other primer is selected from the second set, including a reverse complement of the one primer and the other primer in a set of selected primers; otherwise, if the other primer is selected from the third set, including the one primer and a reverse complement of the other primer in the set of selected primers. The method also comprises: vii) updating a list of target microorganisms to be detected by eliminating from the list target microorganisms having valid amplicons generated by any combination of primers in the set of selected primers; and viii) repeating steps ii) through vii) until a detectable amplicon has been generated by all target microorganisms to be detected.

According to a third aspect, a method for identification of primers suitable for detection of targets and, in particular, target microorganisms is disclosed. The method comprises the steps of: i) identifying a first set of candidate oligonucleotides present in at least one of the target microorganisms; ii) sorting the candidate oligonucleotides of the first set by number of target microorganisms in which they occur; and iii) selecting a most frequently occurring oligonucleotide as one primer. The method further comprises: iii) for all target microorganisms containing the one primer, identifying a second set of candidate oligonucleotides within an upstream or downstream distance range of the one primer; iv) sorting the candidate oligonucleotides of the second set by number of target microorganisms in which they occur; and v) selecting a most frequently occurring oligonucleotide from the sorted candidate oligonucleotides of the second set as another primer. The method also comprises: vi) if the other primer is downstream of the one primer, including the one primer and a reverse complement of the other primer in a set of selected primers; otherwise, if the other primer is upstream of the one primer, including a reverse complement of the one primer and the other primer in the set of selected primers. The method still further comprises: vii) updating a list of target microorganisms to be detected by eliminating from the list target microorganisms having valid amplicons generated by any combination of primers in the set of selected primers; and viii) repeating steps ii) through vii) until a detectable amplicon has been generated by all target microorganisms to be detected.

According to a fourth aspect, a method for identification of primers suitable for detection of target microorganisms. The method comprises the steps of: i) identifying a set of candidate oligonucleotides present in at least one of the target microorganisms; ii) sorting pairs of the candidate oligonucleotides of the set by number of target microorganisms in which they occur within a predetermined distance from each other; iii) selecting the most frequently occurring pair as a pair of primers; and iv) including the pair of primers in a set of selected primer pairs. The method also comprises: v) updating a list of target microorganisms to be detected by eliminating from the list target microorganisms having valid amplicons generated by any pair in the set of selected primer pairs; and vi) repeating steps ii) through v) until a detectable amplicon has been generated by all target microorganisms to be detected.

According to a fifth aspect, set of probe polynucleotides, and in particular a set of primers, is disclosed. The polynucleotides are identifiable by the methods herein disclosed.

According to a sixth aspect, a composition comprising a set of probe polynucleotides, and more particularly a set of primers, of the present disclosure is disclosed, wherein the polynucleotides are comprised in the composition together with and a suitable carrier, vehicle and/or auxiliary agent.

According to a seventh aspect, a method to detect a set of target microorganisms in a sample is disclosed. The method comprises: identifying the set of target microorganisms, each target microorganism of the set of target microorganisms comprising a target polynucleotide; and identifying a set of probe polynucleotides, in particular primers, suitable for identification of the set of target microorganisms with one of the methods herein disclosed. The method further comprises: contacting the identified set of probe polynucleotides with the sample for a time and under condition to allow formation of a probe polynucleotide-target-polynucleotide complex, thus providing a set of probe-polynucleotide-target-polynucleotide complexes; detecting the set of probe polynucleotide target polynucleotide complexes; and comparing the set of detected probe-polynucleotide-target-polynucleotide complexes with a predetermined set of probe-polynucleotide-target polynucleotide complexes, each predetermined probe-polynucleotide-target polynucleotide complex of the predetermined set of probe-polynucleotide-target polynucleotide complexes associated with a target microorganism of the set of target microorganisms.

According to an eighth aspect, a method to identify an unknown microorganism to be included in a set of microorganisms is disclosed. The method comprises: identifying the set of target microorganisms, each target microorganism of the set of target microorganisms comprising a target polynucleotide; and identifying a set of probe polynucleotides, in particular primers, suitable for the identification of the set of target microorganisms with one of the methods herein disclosed. The method further comprises: contacting the identified set of probe polynucleotides with the sample for a time and under condition to allow formation of probe-polynucleotide-target polynucleotide complex, thus providing a set of probe-polynucleotide-target polynucleotide complexes; and detecting the set of a probe-polynucleotide-target-polynucleotide complexes. The method also comprises comparing the set of detected a probe-polynucleotide-target polynucleotide complexes with a set of predetermined probe-polynucleotide-target polynucleotide complexes, each predetermined probe-polynucleotide-target polynucleotide complex of the predetermined set of probe-polynucleotide-target polynucleotide complexes associated with a target microorganism of the set of target microorganisms; and identifying a detected probe-polynucleotide-target polynucleotide complex that cannot be associated with any predetermined probe-polynucleotide-target polynucleotide complex of the set of probe-polynucleotide-target polynucleotide complexes, the identified detected probe-polynucleotide-target polynucleotide complex associated with the unknown microorganism.

According to a ninth aspect, a system for detecting a set of targets and in particular target microorganisms, in a sample and/or for identifying unknown microorganisms to be included in a set of microorganisms is disclosed. The system comprises: a set of probe polynucleotide, in particular primers herein disclosed; and a reagent for providing and/or detecting a complex of said probe polynucleotides with target polynucleotides of said targets.

The probe polynucleotides, compositions, methods and systems herein disclosed allow multiplex detection of a set of microorganisms comprising highly divergent target microorganisms. In particular, the primers, compositions, methods and systems herein disclosed, can be used to detect a set of microorganism including some divergent target microorganisms such as RNA virus genomes of a single species or gene homologues across species, as well as target microorganisms with little nucleotide sequence conservation.

The probe polynucleotides, compositions, methods and systems herein disclosed further allow detection of a set of microorganisms comprising a large and possibly diverse group of microorganisms, using a near-minimal multiplex-compatible set of primers capable of amplifying target sequences in any microorganism of the set of microorganisms at issue (universal primers). In particular, methods and systems herein disclosed allow predicting primer sets for all available complete genomes or segments for every viral family, as well as separate primer sets for several highly diverse species of RNA viruses.

The probe polynucleotides, compositions, methods and systems herein disclosed allow a strategy of detection by PCR amplification with universal primers followed by limited sequencing, fragment length measurement, base composition, or other amplicon-characterizing method, of just a few amplicons per organism which can be used for a fast, cheap, and advantageous for high throughput viral surveillance and discovery.

The probe polynucleotides, compositions, methods and systems herein disclosed, allow use of primers selected to satisfy requirements imposed by the experimental design of choice, such as avoidance of primer-dimers or homodimers formation, isothermal $T_m$'s to improve efficiency of multiplex detection, and allowable GC % range.

The probe polynucleotides, compositions, methods and systems herein disclosed allow detection of a set of microorganisms including a high number of diverse microorganisms with approaches that do not require multiple sequence alignment to be performed.

The probe polynucleotides, compositions, methods and systems herein disclosed can be used in biowarfare detection applications, in particular for identifying, detecting, and monitoring bio-threat agents that contain nucleic acid signatures, such as spores, bacteria, viruses etc.

The probe polynucleotides, compositions, methods and systems herein disclosed can also be used in biomedical applications, in particular for (a) tracking, identifying, and monitoring outbreaks of infectious disease including emerging, previously unidentified and genetically engineered pathogens; and/or (b) automated processing, amplification, and detection of host or microbial and viral DNA or RNA in biological fluids for medical purposes.

The probe polynucleotides, compositions, methods and systems herein disclosed can further be used in forensic applications, in particular for automated processing, amplification, and detection of DNA in biological fluids for forensic purposes.

The probe polynucleotides, compositions, methods and systems herein disclosed can also be used for verification of food and beverage safety and in particular for (a) automated food testing for bacterial or viral contamination; and/or (b) high throughput genetic screening for drug discovery and novel therapeutics The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 8 shows an example of output files from find_amplicons.pl, which compares a list of multiplexed primers to a file of sequences.

FIG. 17 shows a block diagram illustrating the fraction blast hits in target and non-target families for amplicons generated using specific amplification with the universal 10-mer primers for a selection of newly emerged viruses.

FIG. 18 shows a block diagram illustrating the average number blast hits in target and non-target families for amplicons generated using specific amplification with the universal 10-mer primers for a selection of newly emerged viruses.

Figure 1:
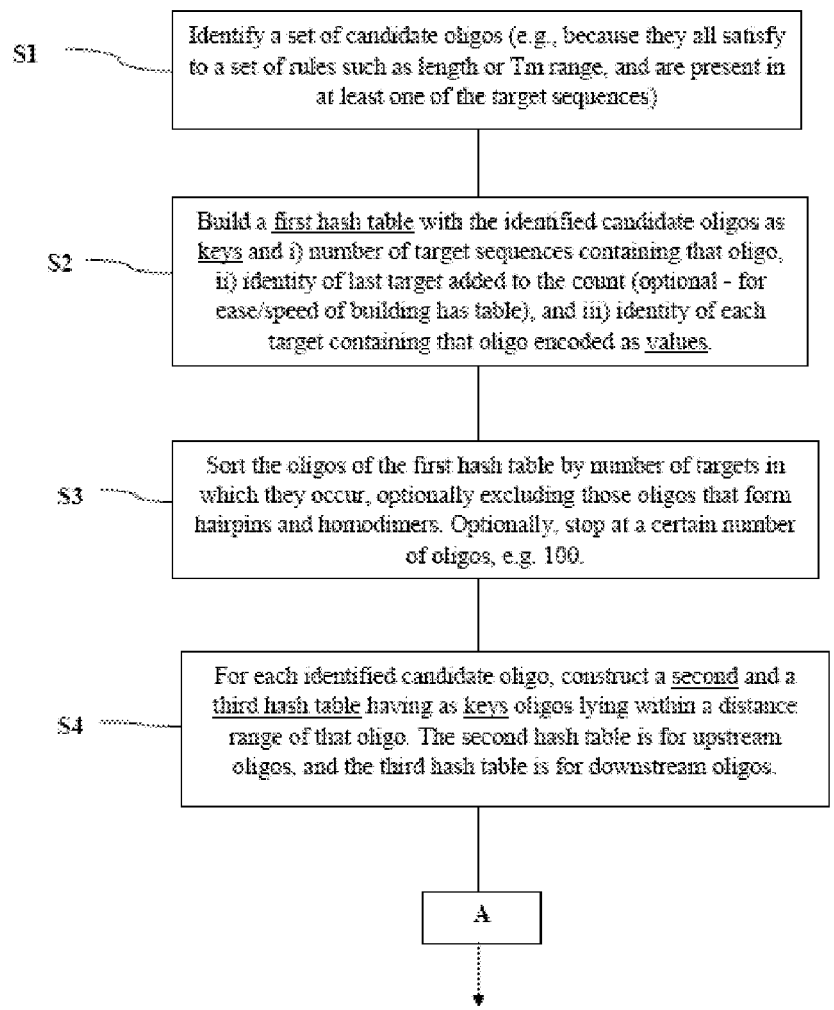
FIGS. 1 to 3 show a first exemplary algorithm to identify probe polynucleotides according to an embodiment herein disclosed.

The present specification also contains appendices A to E, each of which makes part of the present specification and is incorporated by reference in its entirety.

DETAILED DESCRIPTION

Primers, compositions, methods and systems are herein disclosed that can be used for detection and/or identification of targets, and in particular microorganisms, in a sample.

The term "probe" as used herein indicates a hybridization probe, i.e. a polynucleotide of variable length, which is used to detect another polynucleotide (herein also target polynucleotide) having a nucleotide sequence that is complementary to the sequence in the probe. The probe thereby hybridizes to single-stranded nucleic acid (DNA or RNA) whose base sequence allows probe-target base pairing due to complementarity between the probe and target. Exemplary probe polynucleotides are primers suitable for amplification of target polynucleotides.

The term "polynucleotide" or "nucleic acid" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a different functional group. Accordingly, the term "polynucleotide" includes nucleic acids of any length and DNA or RNA analogs and fragments thereof. A short polynucleotide, typically with 60 or fewer nucleotides is also called a nucleotidic oligomer or oligonucleotide, although there is no strict length criteria for defining an oligonucleotide, and strands up to 200 nucleotides can be called oligonucleotides. Probe polynucleotides may be synthesized via phosphoramidite technology or generated and labeled by PCR amplification or cloning (older methods). In order to increase the in vivo stability of the probe RNA is not used, instead RNA analogues may be used, in particular morpholino.

The term "primer" as used herein indicates a strand of nucleic acid that serves as a starting point for replication of a polynucleotide (herein also template polynucleotide). In particular, a primer is able to hybridize a template strand of the template polynucleotide and allow a polymerase to form on the template strand, an elongating strand that is complementary to said template strand. In several applications, primers are usually 6-36 nucleotides long, most often in the range of 18-30 nucleotides, although it is conceivable to have shorter or longer primers. A primer may be introduced in a reaction mixture as a single strand polynucleotide or a double strand polynucleotide and/or as a precursor polynucleotide that can be then converted into the primer by enzymatic reactions or other reactions identifiable by a skilled person upon reading of the present disclosure.

The term "hybridization" as used herein refers to the process of combining complementary, single-stranded nucleic acids into a single molecule, and in particular an at least partially double stranded polynucleotide wherein bases of each strand are bound to bases of the other strand through hydrogen bonding.

The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "identification" as used herein indicates the process of assigning a new or pre-existing individual name or class name to an individual target or a group of targets, such as compounds or microorganisms. Identification of compounds or microorganisms with individual names (or codes) is usually based on individualistic features uniquely associated with the compound or microorganism. In particular, identification of groups of targets (and in particular of set of targets) is usually based on one or more features uniquely associated with the targets of that group of targets.

The term "target" as used herein indicates an analyte of interest. The term "analyte" refers to a substance, compound or component whose presence or absence in a sample has to be detected. Analytes include but are not limited to microorganisms, polynucleotides and related sequences.

The term "microorganism" as used herein refers to an organism of microscopic or ultramicroscopic size such as a prokaryotic or a eukaryotic microbial species or a virus. The term "prokaryotic" refers to a microbial species which contains no nucleus or other organelles in the cell, which includes but is not limited to Bacteria and Archaea. The term "eukaryotic" refers to a microbial species that contains a nucleus and other cell organelles in the cell, which includes but is not limited to Eukarya such as yeast and filamentous fungi, protozoa, algae, or higher Protista.

The term "bacteria" as used herein refers to prokaryotic microbial species which include but are not limited to Gram-positive and Gram-negative bacteria, *Proteobacteria, Cyanobacteria, Spirochetes* and related species, *Planctomyces, Bacteroides, Flavobacteria, Chlamydia*, Green sulfur bacteria, Green non-sulfur bacteria including anaerobic phototrophs, Radioresistant micrococci and related species, *Thermotoga* and *Thermosipho thermophiles*.

The term "virus" refers to a sub-microscopic infectious agent that is unable to grow or reproduce outside a host cell. Each viral particle, or virion, consists of genetic material, (polynucleotides such as DNA or RNA), within a protective protein coat called a capsid. The capsid shape varies from simple helical and icosahedral (polyhedral or near-spherical) forms, to more complex structures with tails or an envelope. Viruses infect all cellular life forms and are grouped into animal, plant and bacterial types, according to the type of host infected. Examples of viruses associated with human diseases include but are not limited to influenza, Ebola, AIDS, avian influenza and SARS.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

In several embodiments, the methods comprise identifying a set of microorganisms to be detected. The wording "set of" as used herein with reference to microorganisms, primers, polynucleotides or other analytes indicate a group including one or more of said analytes. Accordingly, identification of the set of microorganisms to be detected can be performed by assigning a new or pre-existing name to a group of microorganisms that share one or more features uniquely associated with the microorganisms of the group of microorganisms that forms the set to be detected.

In several embodiments, the methods herein disclosed comprise identifying a set of rules to be satisfied by target sequences. The rules of the set of rules can in particular be directed to control base pairing between probe polynucleotide and target polynucleotide and the specificity of related hybridization reactions. The wording "specific" "specifically" or "specificity" as used herein with reference to the binding of a molecule to another, such as polynucleotide hybridization, refers to the recognition, contact and formation of a stable complex between the molecule and the another, together with substantially less to no recognition, contact and formation of a stable complex between each of the molecule and the another with other molecules. The term "specific" as used herein with reference to a molecular component of a complex (e.g. a nucleic acid strand of a double stranded polynucleotide), refers to the unique association of that component to the specific complex which the component is part of. In some embodiments, the set of rules is identified to maximize the specificity of the hybridization between probe nucleotides and target polynucleotides.

The target polynucleotides can then be selected by selecting one or more polynucleotides that is comprised in at least one microorganism of the identified set of target microorganisms, and that comprises a target sequence satisfying to the set of rules.

In some embodiments, probe polynucleotides, and in particular primers, that are suitable for detecting and/or identifying any microorganisms of a set of target microorganisms (herein also universal primer) are identified by reverse complementing the one or more target polynucleotides of the identified set of target polynucleotides.

The wording "reverse complement" as used herein indicates the negative sense, minus strand or complement of a double stranded polynucleotide, that (a) can hybridize to the positive sense, or plus strand of the same double stranded polynucleotide, and (b) is provided in the 5' to the 3' direction. The word "complement" indicates that the sequence is such that where there is an A in the plus strand, there is a T in the complement, and where there is a C in the plus strand, there is a G in the complement, and vice versa. The word "reverse" indicates that the minus or complement strand is given in the 5' to 3' direction, so that its sequence is the reverse of the complement to the plus strand.

In some embodiments, an experimental design of choice is selected in view of the set of rules to be satisfied by target sequences to further control the specificity of polynucleotide hybridization. In particular, in some of those embodiments, the experimental design is selected to maximize the specificity of said hybridization.

In some embodiments, the probe polynucleotides are primers and the set of target polynucleotides comprises two or more target polynucleotides.

In some embodiments, identifying a set of target polynucleotides can be performed by identifying a first target polynucleotide and a second target polynucleotide in at least one microorganism of the set of target microorganisms. In particular, the second target comprises a target sequence that satisfies to a rule requiring that the detection of the microorganism is performed by the combined use of the second target polynucleotide and the first target polynucleotide (e.g. as primers in a PCR or other amplification reactions). In some of those embodiments the set of probe polynucleotides is formed by primers and includes a pair of primers identified by complementing target sequences of the first target polynucleotide or the second target polynucleotide.

In some of those embodiments, at least one of the first and the second target polynucleotides can be further identified in one or more additional target microorganisms different from the initial target microorganism. One or more additional target polynucleotides that comprise one or more additional target sequences can then be identified in the additional target microorganisms. In particular the additional target sequences of the additional target polynucleotide satisfy to a rule that requires that the detection of the additional target microorganisms is performed by the combined use of the additional target polynucleotides and at least one of the first target polynucleotide and the second target polynucleotide. In some of those embodiments, the set of primers includes a first pair of primers identified by complementing target sequences of the first target polynucleotide or the second target polynucleotide and a second pair of primers identified by complementing target sequences of at least one of the first target polynucleotide and the second target polynucleotide and target sequences of the one or more additional target polynucleotides.

In other embodiments at least a first additional target polynucleotide and a second additional target polynucleotide can be further identified in at least a second additional target microorganism of the set of target microorganisms.

The first and second additional target polynucleotide are selected to satisfy a rule requiring that detection of the second additional target microorganism is performed by the second additional target polynucleotide in combination with the at least first additional target polynucleotide. In some of those embodiments, the set of primers includes a first pair of primers identified by complementing target sequences of the first target polynucleotide or the second target polynucleotide and an at least second additional pair of primers identified by complementing target sequences of the first additional target polynucleotide and the second additional target polynucleotide In some embodiments, the identification of suitable primers to detect and/or identify target microorganisms can be performed according to the following steps.

In a first step, a set of acceptable primer candidates is identified. In some embodiments, the first step is performed by reverse complementing a set of target polynucleotides that a) are common to microorganisms of the set of microorganisms to be detected and that b) satisfy the rules of the identified set of rules, as illustrated in the exemplary procedure of Example 6, later discussed.

In particular, in some embodiments, as illustrated in the exemplary procedure of Example 1, later discussed, once certain rules/specifications of experimental design of choice (e.g. desired length, Tm, lack of homopolymer strings etc) are predetermined (e.g. to allow an effective multiplexed detection), a set of polynucleotides that satisfy the predetermined specifications (or parameters) and are common to all or part of the microorganisms of the set of microorganisms to be detected, can be selected. In some embodiments, identification of conserved primers that are also target specific can also be performed, for example with the procedure exemplified in Example 2, later discussed.

In other embodiments, illustrated in the exemplary procedure of Example 3, later discussed, common polynucleotides that occur in all or part of the microorganisms of interests are first identified, the specifications of choice can then be set and the common oligonucleotide matching the desired specification selected.

In all of those embodiments, the target polynucleotides to be used in the identification of the primers herein described are usually identified on the basis of the set of target microorganisms to be detected/identified as illustrated in the exemplary procedures of Examples 4 and 7, later discussed.

In a second step, a set of primer pair is defined on the basis of the acceptable primer candidates identified by the first step. In particular, the set of primer pairs is selected to include primer pairs that allow amplification of target polynucleotides in any microorganisms of the set of microorganisms, as illustrated in the exemplary procedure of Example 6, later discussed.

In some embodiments, the selection of the primer pair is performed by selecting a first primer pair that amplifies at least one target polynucleotide selected according to the first step. Further primer pairs can then be identified by selecting primer pairs that amplify target polynucleotides which are not amplified by other primer pairs until target polynucleotides from all microorganisms of the set of microorganisms to be detected can be amplified. In particular, the primers of each pair can be identified by identifying a first candidate primer and a second candidate primer located upstream or downstream the first candidate primer in target polynucleotides of two or more of the microorganisms to be detected at a distance that allow amplification according to the amplification technique of choice. In some embodiments, all primers of the selected primer pairs are also compared against all targets to be detected by allowing any combination of primers so that primer pairs can be optimized to minimize the number of primers necessary to obtain at least one detectable amplicon from every one of the targets.

The terms "amplify" and "amplification", as used herein with reference to target polynucleotides, indicate a procedure for isolating and exponentially amplifying (e.g. through replication of) a fragment or sequence of a polynucleotide. Exemplary procedures that can be used to amplify a polynucleotide and in particular a target polynucleotide include but are not limited to Polymerase Chain Reaction (PCR), Rolling circle amplification (RCA), Ramification extension amplifying method (RAM), Helicase-dependent amplification (HAD), Abscription (Abortive Transcription), Cycling Probe Technology, Ligase Chain Reaction, Linked Linear Amplification, Looped-Mediated Isothermal Amplification (LAMP), Single Primer Isothermal Amplification (SPIA), Split Promoter Amplification Reaction (SPAR), Strand Displacement Amplification (SDA), and Multiplex Ligation Probe Assay (MLPA).

The term "amplicon" as used herein indicates pieces of a polynucleotide formed as the products of an amplification event. For example, amplicons can be formed via polymerase chain reactions (PCR), ligase chain reactions (LCR) and other procedures for amplifying a polynucleotide identifiable by the skilled persons upon reading of the present disclosure.

Exemplary procedures to perform the identification of primer pairs are illustrated in FIGS. 1 to 3, FIGS. 4 to 6 and FIG. 7 and further exemplified in Examples 1, 3 and 6. Degenerate bases may be included in primer sequences, allowing sequence variation in the target sequences recognized, or hybridized, by the primer. These procedures can be implemented by software and executed by a processor on a computer.

In some embodiments, the method to identify primers herein described can be used for identifying primers particularly suitable to perform multiplexed detection of target microorganisms. In those embodiments the method is also indicated as Multiplex Primer Prediction (MPP) method or software algorithm. The MPP can be used to build multiplex compatible primer sets for large, diverse sets of target sequences.

In some embodiments, the primer identification method herein disclosed, and in particular the MPP, can be used to identify primers suitable to detect and/or identify microorganisms (such as viruses) with high levels of intraspecies sequence variation, which often slip past PCR-based detection if the sequences of some isolates do not contain a match to the specific primers used.

In some embodiments, the MPP can be used to design multiplex primer sets for amplifying homologues in a gene family. In those embodiments, input sequences to MPP could be provided by gene sequences and optionally a small region up- and down-stream of the gene to consider for primer selection, rather than whole genomes as Applicants have demonstrated in the procedures illustrated in the Examples section. A user can specify an appropriate amplicon length range to ensure amplification of an adequate span across the gene.

In some embodiments, the primer identification method and in particular the MPP could also be used to design multiplex primer sets for unrelated target sequences, for example, multiple bacterial and viral species or gene families, in a single reaction. Since no sequence alignment is required, there is no need for any sequence conservation among targets. Combined with a downstream method to identify the amplicons produced, such as hybridization, fragment lengths, or sequencing, MPP is the only available tool to do de novo design of multiplex compatible primer sets to amplify unrelated target sequences in a single PCR.

In various embodiments, the primer identification method and in particular MPP allows design of a large number of diverse primers in a highly scalable (see in particular Example 11, later described), automated fashion (see Example 5, later described) that does not require multiple sequence alignment (see Example 5). In particular, the MPP can be used to design universal primer sets to amplify all available genomes from predetermined sets of microorganisms such as viral families, as well as to generate primer sets for several diverse species such as foot-and-mouth disease virus, influenza, Norwalk virus, and HIV-1. More particularly, in some embodiments, an MPP algorithm is based on conserved k-mer subsequences, requiring no multiple sequence alignments, where multiplex-compatible primer sets are built up de novo as illustrated in the procedures described in the Examples section. In some embodiments, the code may be run from a web interface after uploading an input fasta file of target sequences and selecting parameter values like primer length and $T_m$ and amplicon length ranges, or the source code may be downloaded and run locally.

In some embodiments, exemplified by the procedure illustrated in Example 5 over 25 thousand Orthomyxoviridae sequences were used as input in one run, as well as all Poxviridae sequences, many of them ~200 Kb long. In other embodiments, exemplified by the procedure illustrated in Example 6, later described, runs can be performed using all available viral genomes from all families simultaneously as the input. For many target sets, such as those including all the genomes of a species, predicting a universal primer set usually requires only minutes. With extremely large, highly diverse target sequence sets such as all Orthomyxoviridae sequences, a primer prediction run may take days. Memory requirements can be reduced for example by representing oligonucleotide sequences as bit vectors, with each nucleotide coded as a bit instead of a byte, by using suffix arrays to track all candidate oligonucleotides and their frequencies in the targets, and/or by ranking the primer candidates by frequency. For the top ranked primer candidates, the code can use again suffix arrays or suffix trees to determine oligonucleotide locations in each target sequence. The code can also allow degenerate primers or primers with a limited (user specified) number of mismatches to targets (e.g. using hamming or edit distance options for suffix array calculations).

The sets of probe polynucleotide, and in particular primers, identifiable with the identification method herein described include but are not limited to universal primer sets for all viruses, for each viral family, as well as for several species and serotypes, including influenza, HIV-1, foot-and-mouth disease, and Norwalk viruses and other viruses such as the ones indicated in Example 5, later described, and universal primers for gene families, or other target sets for which sequence data is available.

The number of primers in a universal set depends on the $T_m$ and primer length requirements, as well as the number and diversity of target sequences. In particular, in some embodiments, MPP, in contrast to some prior art techniques, generates non-degenerate primer sets predicted to work in multiplex, to avoid primer dimers, and it does not require any sequence alignment or labor-intensive manual steps to downselect from among multiple candidates or design primers to detect outlying targets.

In some embodiments, sets of primers for detecting and/or identifying viral family include almost 2000 10-mer primers, or ~3700 18-mer primers, as shown in the exemplary procedure of Example 6, later described. Relaxing melting temperature constraints, allowing isothermal primer length variation, or including all primers in a single, highly multiplexed reaction rather than as a series of smaller multiplexes reduces the number of primers required for universal amplification by 20-80%, although these changes would impose greater empirical demands for successful multiplexing.

In some embodiments, universal primer sets consisting of about 7 to about 30 base pair nucleic acid strands can be used to amplify sequences of target viral DNA/RNA as illustrated in the procedure exemplified in Examples 5 and 6. These primer sets can be designed to amplify specific nucleic acid sequences of all viral complete genomes sequenced to date, as well primer sets designed separately for various subgroupings of the viruses, including for each of the viral families (currently 70 virus families with available full genome or full segment sequence data). In embodiments wherein the primer size is fixed at 10 bases (10-mer), between 2 and <700 primers are required in family-level universal sets. The number of primers in a family's set increases with the number of available genomes for that family, as well as the diversity of the family. Sequences for representative sets of these primers are given in Appendix A incorporated herein by reference in its entirety. Examples of primer sets have been provided for each viral family, generated with parameters as indicated in Example 5.

Accordingly, in some embodiments the set of probe polynucleotides can include the sets illustrated in Appendix A (which makes part of the presented specification and is incorporated herein by reference in its entirety), a combination thereof or variants thereof. More particularly, set of primers herein disclosed can comprise a polynucleotide having a sequence selected from the group consisting of SEQ ID NO: 1 to SEQ ID NO:11,333 or a degenerate sequence thereof, wherein the term "degenerate" is used to identify sequences that have at least one degenerate position, i.e. a position which has an ambiguity of one or more bases, with respect to the original sequence while maintaining the ability to hybridize (under the same or other reaction conditions) the same target sequences of the original sequence. More particularly, set of primers can be used for detection of viral families and/or specific viruses as indicated in the Examples and in Appendix A, wherein various combinations of polynucleotides from the same or different sets indicated in the Examples or in Appendix for a certain microorganism or group of microorganism are included in the scope of the present disclosure.

Other primer sets are possible, and can be generated using the code provided in Appendix E, modifying the parameters as desired by the user.

In some embodiments, a probe polynucleotide set identified with the primer identification method herein described can be included in a composition together with a suitable carrier, vehicle or auxiliary agent.

The polynucleotides identified with the identification methods herein described and or the related compositions can be used in a method to detect microorganism of a set of microorganisms in a sample wherein the identified set of polynucleotides is contacted with the sample for a time and under conditions to allow formation of a probe polynucleotide-target polynucleotide complex which can be formed by amplicons in case of amplification of target polynucleotides of the set of target microorganisms with primers. The set of probe-target complexes (and in particular of target amplicons) thus provided can be detected and compared with a predetermined set of probe polynucleotide-target polynucleotide complexes, associated with a target microorganism of the set of target microorganisms.

In some embodiments, the probe polynucleotide identified with the identification methods herein disclosed can be used to identify new and previously unknown microorganism. In those embodiments, the unknown microorganism is identified by identifying at least one probe polynucleotide-target polynucleotide complex that cannot be associated with any predetermined probe-polynucleotide-target polynucleotide complexes of the predetermined set of probe polynucleotide-target polynucleotide complexes. In particular, in those embodiments the identified probe polynucleotide-target polynucleotide complex is associated with the unknown microorganism.

In some of those embodiments, the probe polynucleotides are primers. In particular, previously unknown microorganisms of the set of microorganisms are identified using a primer with a length of less than 11 bases (see simulation procedure exemplified in Example 10, later described).

More particularly, some embodiments are based on the observation that short primers are more likely to be conserved among both known, sequenced microorganisms and unknown or unsequenced microorganisms. Amplicons generated using short primers that do not match amplicons predicted based on known, sequenced microorganisms, indicate that an unknown organism is present (see Example 10). The novel amplicons can be further characterized, such as by amplicon sequencing and comparison to existing sequence databases. Amplicons can also be exploited to further characterize the unknown, for example by designing primers based on the novel amplicon, and using them to amplify or sequence additional regions from the sample containing the novel organism.

In some embodiments, the method to detect/identify a set of microorganisms is performed by contacting the set of identified probe polynucleotides (and in particular primer pairs) with the sample in a single reaction vessel, (see Example 5, specifically the examples indicated as "no Bins"). In particular, all probes (and in particular primers) for a given target set of sequences are intended to be mixed in a single multiplex reaction for creating an amplicon from any one of those target sequences (see Example 5). The probes going into the multiplex reaction can be computationally selected to avoid probe dimers.

In other embodiments, the method to detect/identify a set of microorganisms is performed by subdividing an initial sample in several (even millions or billions) of discrete sub-samples to allow analysis of every individual microorganism in the set in parallel as illustrated in the exemplary procedure of Example 14 wherein the probes are primers. In particular, in view of reaction kinetics and thermodynamics created by multiplexing an enormous number of primers in order to simultaneously amplify a huge number of different targets, in some embodiments, the sample can be divided into bins based on the set of microorganisms of interest (e.g. a viral family of interest), or alternatively based on the multiplex compatibility of the primers involved (the approach used in the procedure of Example 6.

In those embodiments, each subsample would only contain a smaller set of probes, limiting the complexity of the hybridization and detection reactions. In some of those embodiments the hybridization is also performed using small primers (e.g. of length 5-11 nucleotides), which are likely to hybridize any target (including unknowns), versus using larger oligos with more specificity. Use of smaller probes, and in particular smaller primers, requires a more limited multiplex compared to other embodiments, since shorter probes are more likely to be conserved among more target sequences, meaning that in the exemplary case in which probes are primer, fewer primers in total should be required to generate amplicons from every target. However, short primers may also reduce the amplicon resolution since for some microorganisms the primers in a set may amplify dozens to thousands of amplicons, making it difficult to differentiate or further characterize each fragment when it is part of a more complex mixture of sequences (see Examples 8, 13 and 14).

In some embodiments, hybridization and detection (e.g. through amplification and sequencing) of a few, randomly chosen fragments can be performed. In particular, Applicants performed simulations to determine how the length and number such fragments affect the ability to classify that virus as to its correct family, and found that sequencing a few 100-mer fragments is likely to provide correct family identification, and is likely to provide more information than sequencing a single fragment that is ten times longer (see Examples 9, 10, and 12). A possible explanation that is not intended to be limiting of the scope of the disclosure is that in some of those embodiments the 100-mer regions could be more dispersed across the genome of the target than a single, longer region, and this may increase the probability of including a region that is characteristic of the appropriate family. However, in some of those embodiments a sophisticated empirical strategy might need to be employed to separate out one or a few amplicons for sequencing per genome, since one would not have a specific sequencing primer if fragments are selected randomly. One could imagine that pyrosequencing [ref 15] methods might be adaptable to such a strategy, with modification so as to rapidly amplify only a few, randomly selected fragments from each of many samples rather than more deeply sequencing a single sample. Cost and speed might be the advantages of sequencing a limited number of fragments rather than more deeply sequencing many oligonucleotide fragments from a sample, so long as a sufficient number are sequences so as to characterize the organism(s) in the sample to the desired level.

In other embodiments, a specific amplification (directed to amplify specific predetermined fragments, as opposed to random amplification directed to amply randomly chosen fragments) can be performed e.g. by using short primers of 5-11 nucleotides. In those embodiments, in view of the short length of the primers, it is essential to purify the sample, excluding as much contaminating nucleic acids from eukaryotic and prokaryotic sources as possible, since simulations indicate that sets of short multiplex primers will generate hundreds or thousands of amplicons from a human or typical bacterial genome, overwhelming any viral signal. Alternatively, longer primers can be used, including but not limited to lengths of 17-30 nucleotides, and these can be designed so as to have more specificity to the targets, which should allow less thorough sample purification to eliminate eukaryotic DNA/RNA prior to amplification.

In the methods to detect/identify microorganisms herein disclosed the detected complexes are compared to predetermined complexes associated to microorganisms of the set of microorganisms to identify the microorganism associated to the detected complex. In particular, in embodiments wherein the probes are formed by primers, following amplification of the target polynucleotides, the related amplicons can be detected and then compared with predetermined amplicons associated with known microorganisms to detect the microorganism associated with the amplicon or identify a previously unknown microorganism.

Detection of the probe polynucleotide-target polynucleotide complexes can be performed with techniques identifiable by a skilled person, which can vary in view of the specific probe polynucleotide used in the probe polynucleotide-target polynucleotide complexes. In particular, detection of a probe polynucleotide-target polynucleotide complex can be performed through labels or labeled molecules.

The terms "label" and "labeled" as used herein refers to a probe, primer or other molecule that is capable of being detected. Labels include but are not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" as used herein indicates the signal emitted from the label that allows detection of the label, including but not limited to radioactivity, fluorescence, chemoluminescence, production of a compound in outcome of an enzymatic reaction and the likes.

For example, in some embodiment, detection of a probe polynucleotide-target polynucleotide complex can be performed by labeled probes that can be detected with methods known or identifiable by a skilled person such as Southern blotting RNAase protection or the likes. For example, to detect hybridization of the probe to its target sequence, the probe can be tagged (or labelled) with a molecular marker; commonly used markers are $^{32}P$ (a radioactive isotope of phosphorus incorporated into the phosphodiester bond in the probe DNA) or Digoxigenin, which is non-radioactive antibody-based marker. DNA sequences or RNA transcripts that have moderate to high sequence similarity to the probe are then detected by visualizing the hybridized probe via autoradiography or other imaging techniques. Detection of sequences with moderate or high similarity depends on how stringent the hybridization conditions were applied—high stringency, such as high hybridization temperature and low salt in hybridization buffers, permits only hybridization between nucleic acid sequences that are highly similar and therefore detection of specific complexes, whereas low stringency, such as lower temperature and high salt, allows hybridization when the sequences that are less similar. Hybridization probes used in DNA microarrays refer to DNA covalently attached to an inert surface, such as coated glass slides or gene chips, and to which a mobile cDNA target is hybridized. When the probe polynucleotide is a primer, detection can be performed by detecting products of replication of a target polynucleotide and in particular amplicons.

In other embodiments, wherein the probes are primers, the detection of the amplicon is performed by detecting the lengths of the resulting amplicon fragments determined through a technique such as separation using gradient electrophoresis. In those embodiments, the microorganisms detection is based on the unique electrophoretic banding signature created by the amplification of individual fragments from a given species or strain of virus. Examples of some fragment length distributions detectable using gradient electrophoresis are given in Appendices B-D each of which makes part of the present specification. Additional procedures suitable to detect amplicons and/or perform viral characterization include but are not limited to techniques such as mass spectrometry to estimate base composition (like that used by IBIS T5000) [ref. 4, 22], electrophoretic determination of fragment size distributions, fragment sequence, microarray or other (e.g. Luminex beads, nano bar codes, etc.) hybridization patterns.

An exemplary procedure suitable to detect amplicons for various sets of microorganisms (and in particular viruses) is illustrated in Example 14, later discussed.

Systems for detection and/or identification of target microorganisms are also disclosed. The systems include a set of probes, and in particular primers, herein disclosed alone or in combination with reagents suitable to perform the detection according to the methods herein disclosed.

The systems herein disclosed can be provided in the form of kits of parts. In particular in a kit of parts, one or more primers (in particular, a set of primers) and possibly also other reagents can be comprised in the kit independently possibly included in a composition together with suitable vehicle carrier or auxiliary agents. For example a polynucleotide can be included in one or more compositions alone and/or included in a suitable vector. Also, the primers of the set of primers can be included in a composition alone or together with other primers of the same set. Furthermore, the primers can be included in various forms or compositions that are suitable for use in amplifying target polynucleotides of interest or to detect the polynucleotide of interest with other techniques that do not require amplification of the target. For example, in some embodiments, a labeled primer can be included in the kit to allow detection using techniques identifiable by the skilled person and that vary in view of the label used.

In some embodiments, a labeling molecule can also be included in the kit herein disclosed, that allows detection of the amplicons or the polynucleotide of interest and include but are not limited to labeled polynucleotides, labeled antibodies, other labels identifiable by the skilled person upon reading of the present disclosure.

Additional components can also be included and comprise system reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

Example 1

Algorithm for Calculating Highly Conserved, Multiplexed Primer Sets

To select highly conserved universal primers for a set of targets, Applicants have coded the following algorithm in PERL, provided as Appendix E. The universal set of primers should produce at least one amplicon in each of the target sequences. The process is as follows:

1) First, one identifies all candidate oligos occurring in the target set of sequences that fall in the desired length and $T_m$ ranges (Table 1), do not contain homopolymer strings longer than 4 bases, do not contain non-ATCG bases, and are not composed entirely of dinucleotide repeats. $T_m$'s and free energies (see below) are calculated using Unafold. [ref. 39] Alternative values of any of the parameters in Table 1 may be desired, and can be specified by the user. Alternatively, candidate oligos can be selected based on GC % and length, rather than $T_m$. Alternative methods of calculating $T_m$ and free energies may be used. All parameter settings are provided as examples, and are not exclusive.

TABLE 1

| Parameter | Value |
| --- | --- |
| Minimum $T_m$ | 35° C. * (10-mer) or 55° C. (17-18-mer) |
| Maximum $T_m$ | 50° C. (10-mer) or 70° C. (17-18-mer) |
| $x_{homodimer}$ | −7 kcal/mol |
| $x_{dimer}$ | −7 kcal/mol |
| $x_{hair}$ | −5 kcal/mol |
| $d_1$ | 80 |
| $d_2$ | 620 |

* Throughout, $T_m$ and ΔG are calculated using Unafold with $[Na^+] = 0.2$ M, $[Mg^{+2}] = 0.0015$ M, $T_{anneal} = 30°$ C., strand concentration of each strand of 1e−07 M, and with the "DNA" option. Alternative settings may be employed, as specified by the user.

These candidate oligos are stored in a hash $h_1$ with the oligo sequences as keys (stored as strings, or in another embodiment, stored as bit vectors) and values containing bit vectors composed of the following: the number of genomes containing that oligo, the identity of the last target sequence added to the count (to speed the initial hash construction), and the identities of each target sequence containing that oligo. Target sequences are referenced by number in a lookup table. This representation stores the oligo frequencies efficiently for subsequent calculations, but does not track the location of each oligo in each sequence, to reduce memory requirements. Currently, oligo sequences in the keys are represented as character strings (8 bits/character), although in a future version this will be replaced with storage of A, C, T, and G using only 2 bits each, providing a four-fold memory savings.

2) Second, the oligos are sorted by the frequency of target sequences in which they occur. A set $s_1$ of the 100 most frequent oligos whose homodimer and hairpin free energies exceed $x_{homodimer}$ and $x_{hair}$, respectively, is constructed. Since free energy calculation is relatively time consuming, these are only calculated as needed until the set $s_1$ has been populated with 100 oligos (this number is a tunable parameter that can be set by the user).

3) Next, two more hashes are constructed like the first for each oligo i in $s_1$, using only the subsequences from the original targets that lie within distance range $d_1$-$d_2$ of that oligo $s_{1i}$. One is a hash $h_{2u}$ for the upstream oligos, and the other is a hash $h_{2d}$ for the downstream oligos. After sorting both $h_{2u}$ and $h_{2d}$ by frequency in the target sequences, the oligo j is chosen for each oligo i that occurs most frequently either upstream or downstream, giving the most frequent oligo pairs (i,j). Again, only oligos j with homodimer and hairpin free energies exceeding $x_{homodimer}$ and $x_{hair}$ and (i,j) dimer free energy exceeding $x_{dimer}$ are allowed, so if the most frequent j is not energetically acceptable, the next most frequent j is selected until an acceptable oligo can be found. The most frequent pair (i*,j*) is selected from among all (i,j) pairs. If j* is from $h_{2u}$, then it becomes primer $p_1$ and the reverse complement of i* becomes primer $p_2$, while if j* is from $h_{2d}$ then the reverse complement of j* and i* are used as primers. These primers are added to the reaction bin.

4) Then the list of target sequences yet to be detected is updated, eliminating any with valid amplicons in the specified size range generated by any combination of primers already selected. The values of hash $h_1$ are also updated by subtracting from the oligo frequency counts those targets detected and removing their target identities.

5) The process from steps 2-4 is repeated for the targets not yet detected until all targets have a valid amplicon, adding the constraint at the end of step 3 that primers $p_1$ and $p_2$ must have dimer free energies exceeding $x_{dimer}$ with any primer already selected, in order to be added to the bin. If either primer in the pair is predicted to dimerize with any primer already selected in that bin, then the next most frequent pair (i*,j*) is checked for acceptability as primers, until a suitable pair is found. In step 4, since primers in a bin are intended to be mixed in multiplex, targets can be detected by any combination of primers in any orientation relative to one another, not just those that were selected as a pair. Applicants call these unintended detections "serendipitous hits", and update the list of yet-to-be-detected targets and $h_1$ accordingly.

6) If the option to bin primers in subsets of b primers is selected, primers are added to a bin until that bin contains a maximum of b primers, at which point a new bin is begun. Occasionally, the same primer may be selected more than once in the same bin, paired with a different oligo, resulting in an odd number of primers. Binning primers in small groups avoids exclusion of the most highly conserved oligos because of primer dimer free energy constraints. It also results in fewer amplicons on average per genome, since each reaction bin contains fewer primers than would a larger multiplex of unbinned primers.

In the software release, Applicants also include a script, find_amplicons.pl, to predict all the amplicons that should be generated by a list of (multiplexed) primers mixed with any fasta file of sequences (FIG. 8). For each sequence, all amplicon sequences (for example, SEQ ID NO: 11353, SEQ ID NO: 11354 and SEQ ID NO: 11355 as shown in FIG. 8), their length and position, and the forward primer (for example, SEQ ID NO: 427, SEQ ID NO: 425 and SEQ ID NO: 429 as shown in FIG. 8)+reverse primer (for example, SEQ ID NO: 428, SEQ ID NO: 426 and SEQ ID NO: 430 as shown in FIG. 8) combination to yield that product (or if appropriate an indication that no amplicons are predicted) as well as the reverse complimentary sequences of the forward primers (for example, SEQ ID NO: 11356, SEQ ID NO: 11357 and SEQ ID NO: 11358 as shown in FIG. 8) are printed to an output file. The amplicon sequences facilitate downstream analysis, such as probe design or fragment length or sequence comparisons among the amplified sequences. The script also produces a summary file of the fragment length distributions, or expected banding patterns, and a list of the sequence headers predicted to display each pattern.

Figure 2:
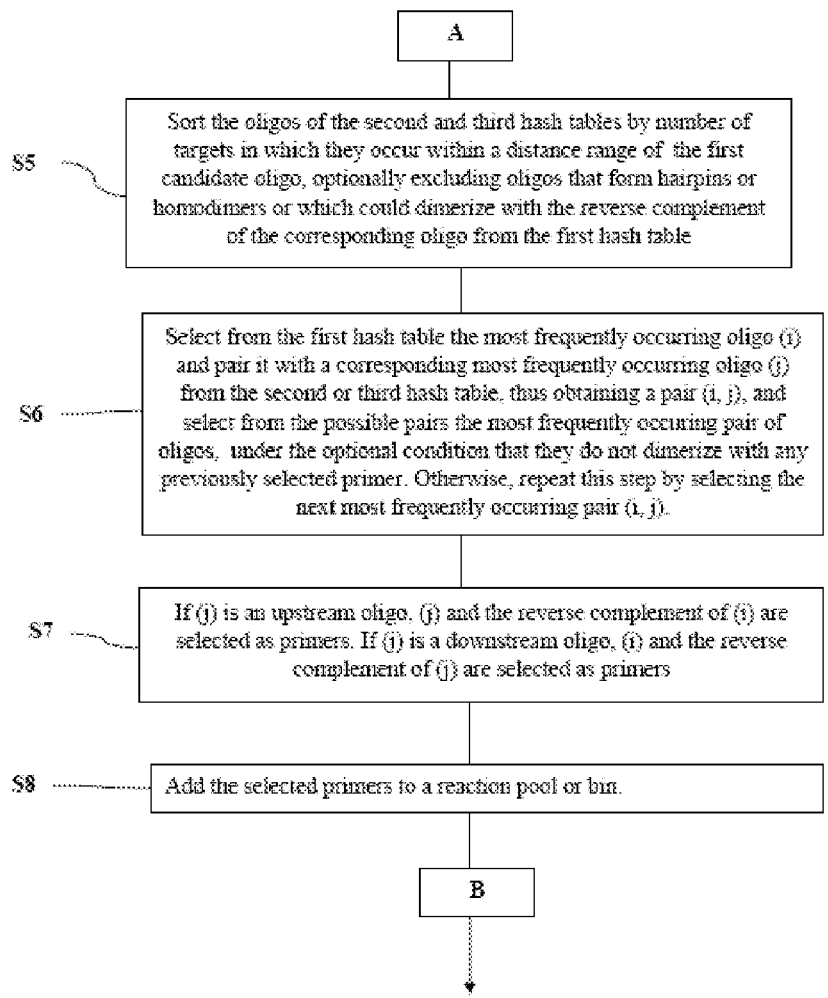
Figure 3:
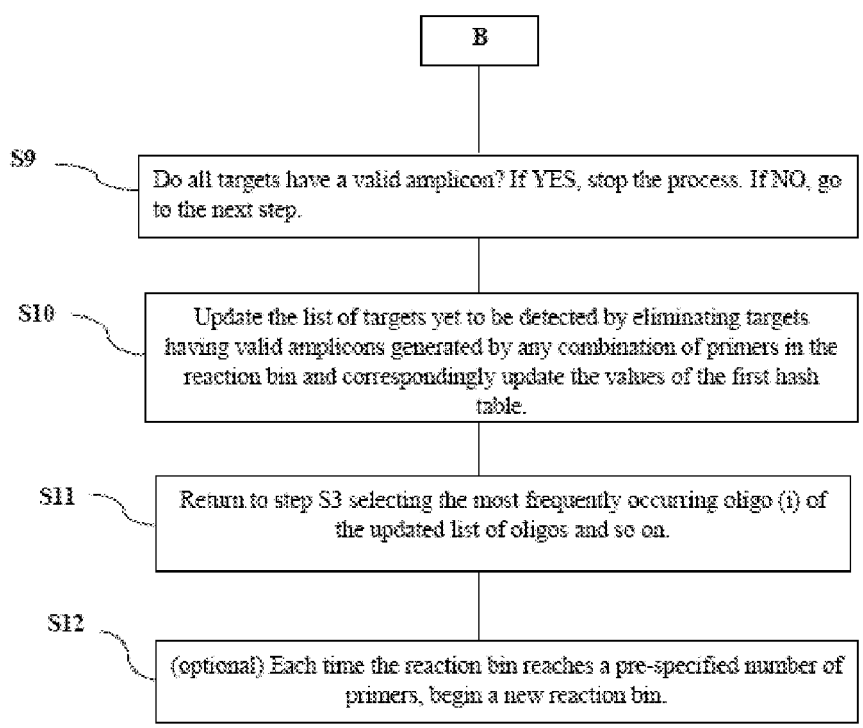

An embodiment of the present disclosure on which Example 1 is based is shown in the flowchart of FIGS. 1 to 3, which show steps S1-S12 for performing a method to identify primers suitable for detecting target microorganisms.

Example 2

Identification of Conserved and Target Specific Primers

The code described in Example 1 focuses on finding conserved primers, and does not require that the primers be family- or species-specific. Thus, organisms outside the target sequence set could also generate amplicons. To ensure that a member of the target group is present using the primers generated using the methods described above requires analysis of the amplicons produced (for example, sequence, base composition, or length). However, if specific as well as conserved primers are required, the simplest approach would be to input a set of target sequences in which all k-mers (where k is the primer length) present in any non-target organism have been replaced by "N"'s.

These non-unique oligos will not be considered as primer candidates, and can be found using, for example, BLAST [ref. 29] or suffix array software such as vmatch (http://www.vmatch.de/). This approach, however, does risk being overly strict by eliminating some potentially successful candidate primers: it takes two primers in proximity to generate an amplicon, so 1) a single non-unique primer, 2) a pair of primers too far apart to actually generate an amplicon in a non-target sequence, or 3) nearby candidate oligos that partially overlap a non-unique stretch of N's might actually work to uniquely amplify members of the target set. Applicants are currently formulating a modified algorithm to address the third of these issues, which after hashing candidate oligonucleotides as described in Example 1 step 1, those oligonucleotides are checked against a nucleotide sequence database of non-target sequences using suffix array software such as vmatch, and candidate oligonucleotides that are not unique to the target sequences (with a user-selected level of 0 or more mismatches or indels by hamming or edit distance) are eliminated from further consideration as candidate primers by eliminating them from the hash h1. In the current version of the MPP of Example 1, all primers sets described in the analyses performed here are conserved, but they were not checked for uniqueness.

Example 3

Algorithm for Calculating Highly Conserved, Multiplexed Primer Sets Meeting Required Specification Primer sets were identified according to the following process.

1) List all acceptable primer candidates: First, all oligos that occur in any of the sequences in the target set are found, where the target set is a set of viral genomes, either all viral genomes or the genomes in a particular family. Only those matching the desired specifications proceed. These specifications can be any or all of the following: length, Tm, and GC % within specified ranges, no homopolymer strings of more than 4 bases (e.g. primers with AAAAA (SEQ ID 11,334) not allowed), and no primers that are composed entirely of a dinucleotide repeat. Applicants have developed code that predicts conserved universal primers that may vary in length but that have isothermal melting temperatures to improve their compatibility in multiplex reactions. Tm's are predicted using our streamlined version of the most accurate software currently available: Unafold®, based on nearest neighbor thermodynamics. As part of a Tech Based Award through the Computations directorate, Applicants improved the speed of Unafold so that it can predict the Tm's of over 100 million oligonucleotides in just hours, making it feasible for predictions for even the largest viral families. In addition, Applicants have implemented a new addition to the algorithm to further aid the prediction of multiplexed primer sets by avoiding primer dimers, homodimers, and hairpins, which compete with the desired reactions of primer-target binding. These undesired reactions can also be predicted using the thermodynamic models in the Unafold software, although these computations are slower, so they are performed later as described below. The location of each primer in each of the target genomes is recorded, even if a given oligo occurs multiple times. Forward versus reverse complements of oligos are also tracked, since it will be important whether a primer will amplify in the forward or reverse direction. The strand that is given as the plus strand in Genbank is arbitrary for double-stranded genomes. To make this memory-intensive process feasible, data is stored as bits rather than bytes, in an efficient hash lookup table. This lookup table contains sequence and positional information of each candidate primer in each of the target genomes. Applicants also have an option in the code to tie the hash to disk, if memory is still limiting. Although that requires longer run times, it does allow larger numbers or longer sets of target genomes to be analyzed, although running the analyses subdivided by viral family does not require tying the hash file to disk.

2) Select the first primer pair: Oligos are sorted by the frequency of presence/absence in the target genomes, and the primer candidate p1 present in the most genomes is selected. The hairpin and homodimer free energy is calculated, and if the oligo passes the user's specifications, then that oligo continues for consideration as p1. If not, it is excluded from further consideration and the next most conserved oligo is selected as p1. Then, for all genomes that contain p1, all oligos within an allowable distance range d upstream (5') of the highest frequency oligo are again sorted by frequency of presence/absence in that same subset of genomes within distance d of p1. This process is repeated for oligos within an allowable distance range d downstream (3') of p1. The oligo p2 that is either upstream or downstream that occurs in the most genomes is selected as a pair with p1, and it is checked for free energies of formation of hairpins, homodimers, and primer dimers with p1. If these free energies are not acceptable, the next most frequent oligo is selected as p2, and so on, until one can be selected that forms neither hairpins nor primer dimers. Oligos that are the reverse complement of one that has already been selected are not permitted, so as to avoid obvious primer dimer formation. If the downstream oligo is chosen, then p1 and the reverse complement of p2 are added to the universal primer set. If instead the upstream oligo is chosen, then the reverse complement of p1 and the existing p2 (not reverse complemented) are added to the universal primer set. Thus, the two primers added should work in a pair as a forward and reverse primer to amplify detectable fragments in the maximum number of target genomes. The distance d is determined by the technology used to detect the bands, e.g. for capillary electrophoresis, bands up to 1500 bp can be discriminated.

3) Determine as-yet-unamplified genomes and find next set of primers. Those genomes that yield a detectable (in the appropriate length range) band from the first two primers are stored in a "detected" pool, and all the oligos in the remaining genomes are re-sorted by the number of as-yet-undetected genomes in which they occur. The oligo p3 occurring in the most genomes is checked for hairpins and dimers, and if acceptable it is selected, and again as in step 2 all oligos within a distance d upstream or downstream of p3 are ranked by frequency and the one with the highest frequency is chosen as p4, as in step 2 determining which oligo should be reverse complemented to serve as a reverse primer of the pair. In selecting all oligos to add to the set of primers, no primers that are predicted to form hairpins or primer dimers (homodimers or dimers with other primers already in the set) are allowed. The primer p4 may be the same as one previously chosen (p1, p2, or p3), in which case the universal primer set increases by only one instead of two primers.

4) All the primers chosen thus far are compared against all of the targets, allowing any combination of primers as the forward or reverse of a pair, and those genomes in which a detectable band appears are stored in the detected pool. The steps 3-4 are repeated on the as-yet-undetected targets until sufficient primers are chosen such that at least one detectable amplicon is generated from every one of the targets.

In view of the number of viral sequence data used to create these primer sets the huge predicted viral diversity on earth, the rapid evolution of RNA and phage viruses, and the lack of cultureable viruses to characterize, it is expected, therefore, that these signatures will evolve following the process defined above at regular intervals. Despite these challenges, Applicants have computationally demonstrated the ability of this initial primer set to identify newly emerging viruses such as Ebola, SARS, Nipah, and Hendra viruses. The electrophoretic banding signatures would be identified as "unknown", or outside the existing banding library for sequenced viruses. These bands could easily be extracted and sequenced for comparison against existing genome libraries. This would create an ever-expanding library of biological viral signatures (based on fragment size) that could be used to rapidly characterize unknown samples.

Figure 4:
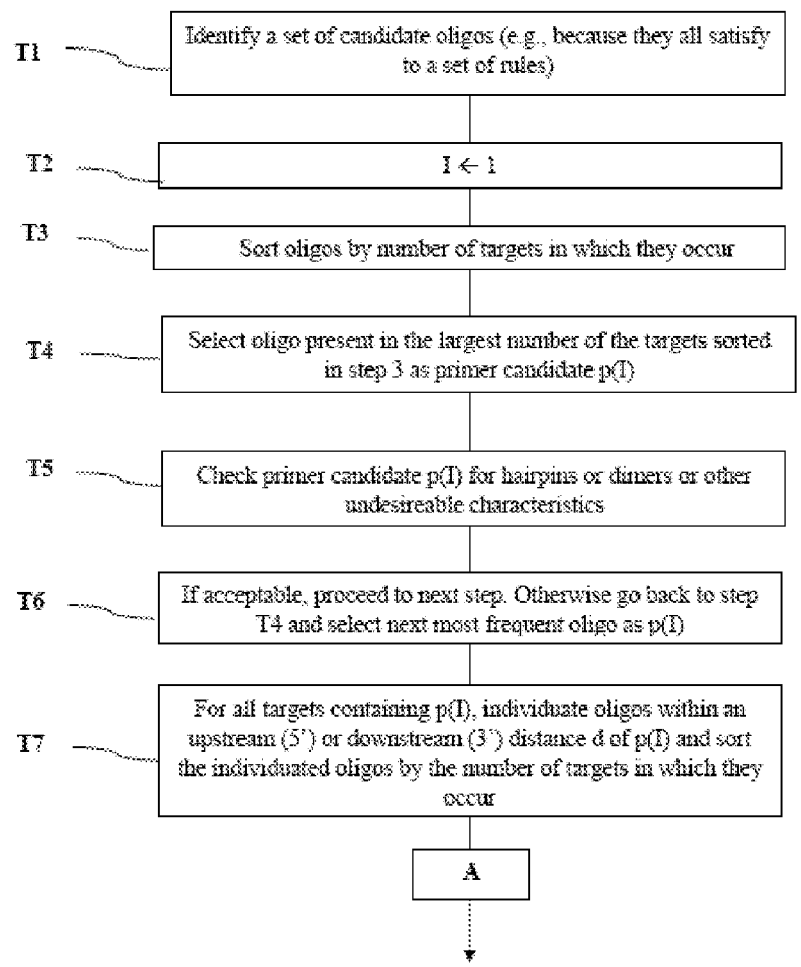
FIGS. 4 to 6 show a second exemplary algorithm to identify probe polynucleotides according to an embodiment herein disclosed.
Figure 5:
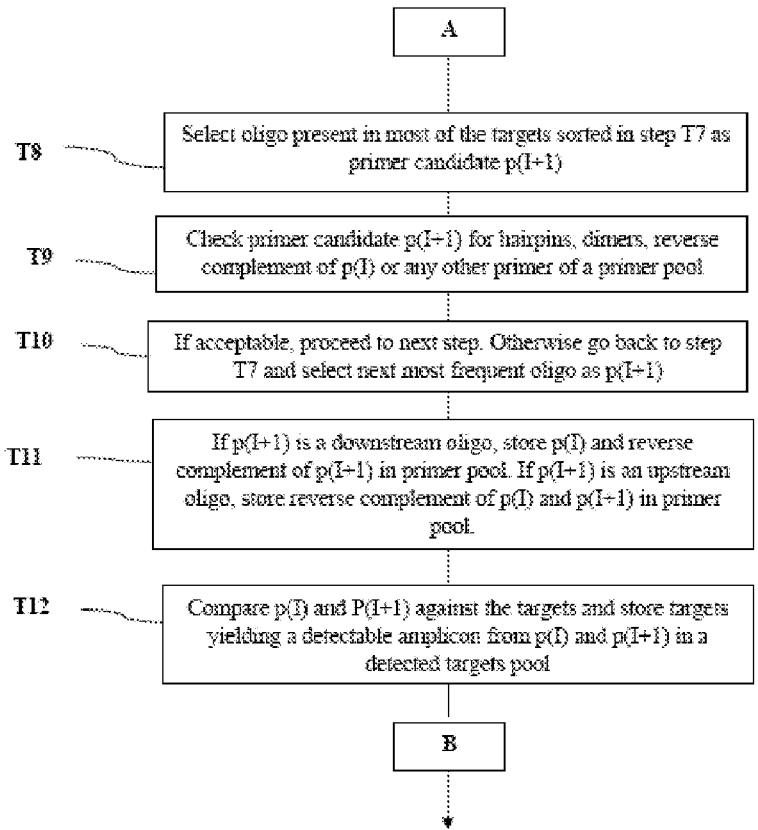
Figure 6:
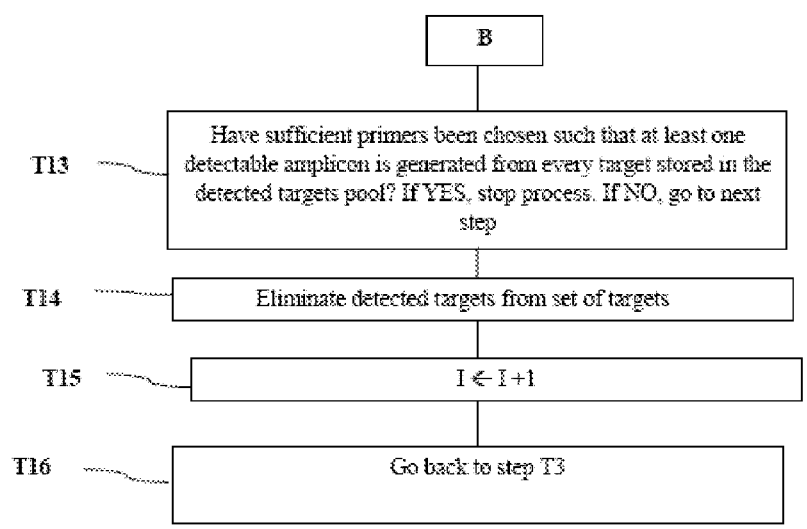

An embodiment of the present disclosure on which Example 2 is based is shown in the flowchart of FIGS. 4 to 6, which show steps T1-T16 for performing a method to identify primers suitable for detecting target microorganisms.

Example 4

Target Sets Used in Calculations of Conserved Primer Sets

Target sets used in this example are the set of all viral complete genomes and complete segments for each viral family, downloaded from publicly available sequence databases (Genbank, Baylor, TIGR) as of Oct. 29, 2007. Partial genomes were not included. Applicants' goal was to generate highly conserved family-level primer sets. There were genome sequences available for 70 of the 72 families, except for Metaviridae and Roniviridae. Draft sequences with multiple contigs were merged into a single sequence entry, with contigs separated by 1000 N's, a stretch sufficiently long (greater than $d_2$ in all but one of our runs) so that primer pairs would not be designed to fall on different contigs, although there were very few draft sequences in contigs where this was necessary. Calculations were performed on a single AMD Opteron 2.4 GHz processor with 16 or 32 GB of RAM. Run parameters are given in Table 1 of Example 1. For family-level primers, Applicants computed primer sets with primers of length 10, for binned primers in groups of b=20 primers per bin. Applicants also computed primers sets assuming unbinned primers (all primers in the set mixed in a single reaction) and removing all $T_m$ constraints.

Next, Applicants computed primers of length 17-18-mers in unbinned reactions with the $T_m$'s and other parameters as specified in Table 1 (see Example 1). Finally, Applicants designed primers of 17-20 bases in groups of 30 primers per bin, primer $T_m$=55-65° C., and with amplicon length ($d_1$ and $d_2$) 100-2000 bp.

Applicants also generated primer sets for several species with high sequence diversity: HIV-1, foot-and-mouth-disease virus (FMDV), Norwalk virus, and Influenza A segments HA and NA. To illustrate the challenges of designing primers from an alignment, Applicants aligned these organisms using MUSCLE [ref. 33] when possible. For the HIV-1 and Influenza A segments HA and NA sequences, MUSCLE ran out of memory before completing. An alternative alignment tool, Clustalw [ref. 31], had completed only a small fraction of the alignment after running for days. So for these large data sets, a random selection of ~35 sequences for each target was aligned with MUSCLE, and this alignment was used to build an HMM (hmmbuild) using HMMer (http://hmmer.wustl.edu/). [ref. 32] The full sequence set was then aligned to the HMM using hmmalign. For Norwalk virus and FMDV, Applicants designed multiplex-degenerate primer sets using Greene SCPrimer [ref. 36] and HYDEN [ref. 38].

Example 5

Primer Sets Suitable for Viral Genome Identification

The number of family-level primers for each family, and the number of genomes available for generating those primer sets, is given in Table 2, for 4 alternative parameter settings.

TABLE 2

| Family | DNA or RNA | Single (s) or double (d) stranded | Number of Genomes or Segments | Tm 35-50, 10-mers, 20 primers/bin, Amplicon length 80-620 | No bins, No Tm or GC % constraints, 10-mers, Amplicon length 80-620 | Tm 55-70, primer length 17-18, no bins, Amplicon length 80-620 | Tm 55-65, primer length 17-20, Bin size = 30, Amplicon length 100-2000 |
|---|---|---|---|---|---|---|---|
| Metaviridae | RNA | S | 0 | 0 | 0 | 0 | 0 |
| Roniviridae | RNA | s | 0 | 0 | 0 | 0 | 0 |
| Barnaviridae | RNA | s | 1 | 2 | 2 | 2 | 2 |
| Bicaudaviridae | DNA | d | 1 | 2 | 2 | 2 | 2 |
| Corticoviridae | DNA | d | 1 | 2 | 2 | 2 | 2 |
| Marnaviridae | RNA | s | 1 | 2 | 2 | 2 | 2 |
| Plasmaviridae | DNA | d | 1 | 2 | 2 | 2 | 2 |
| Globuloviridae | DNA | d | 2 | 2 | 2 | 4 | 4 |
| Lipothrixviridae | DNA | d | 2 | 4 | 2 | 4 | 4 |
| Nimaviridae | DNA | d | 3 | 2 | 2 | 2 | 2 |
| Rudiviridae | DNA | d | 4 | 4 | 2 | 4 | 4 |
| Ascoviridae | DNA | d | 5 | 4 | 2 | 4 | 4 |
| Fuselloviridae | DNA | d | 5 | 4 | 4 | 6 | 6 |
| Hypoviridae | RNA | d | 6 | 4 | 4 | 6 | 6 |
| Phycodnaviridae | DNA | d | 6 | 6 | 4 | 6 | 6 |

TABLE 2-continued

| Family | DNA or RNA | Single (s) or double (d) stranded | Number of Genomes or Segments | Tm 35-50, 10-mers, 20 primers/bin, Amplicon length 80-620 | No bins, No Tm or GC % constraints, 10-mers, Amplicon length 80-620 | Tm 55-70, primer length 17-18, no bins, Amplicon length 80-620 | Tm 55-65, primer length 17-20, Bin size = 30, Amplicon length 100-2000 |
|---|---|---|---|---|---|---|---|
| Tetraviridae | RNA | s | 6 | 8 | 8 | 12 | 12 |
| Asfarviridae | DNA | d | 8 | 2 | 2 | 2 | 2 |
| Chrysoviridae | RNA | d | 8 | 10 | 6 | 15 | 16 |
| Narnaviridae | RNA | s | 8 | 12 | 8 | 16 | 16 |
| Sequiviridae | RNA | s | 8 | 6 | 6 | 8 | 6 |
| Iridoviridae | DNA | d | 9 | 8 | 4 | 14 | 14 |
| Tectiviridae | DNA | d | 10 | 2 | 2 | 4 | 4 |
| Bornaviridae | RNA | s | 11 | 2 | 2 | 2 | 2 |
| Leviviridae | RNA | s | 11 | 8 | 8 | 13 | 14 |
| Birnaviridae | RNA | d | 12 | 12 | 10 | 16 | 16 |
| Cystoviridae | RNA | d | 12 | 14 | 12 | 24 | 22 |
| Astroviridae | RNA | s | 13 | 6 | 6 | 12 | 12 |
| Tymoviridae | RNA | s | 16 | 10 | 8 | 22 | 20 |
| Nodaviridae | RNA | s | 18 | 20 | 16 | 22 | 22 |
| Dicistroviridae | RNA | s | 19 | 20 | 12 | 24 | 24 |
| Inoviridae | DNA | s | 28 | 22 | 14 | 32 | 32 |
| Totiviridae | RNA | d | 29 | 28 | 24 | 46 | 46 |
| Filoviridae | RNA | s | 35 | 6 | 4 | 5 | 6 |
| Comoviridae | RNA | s | 36 | 34 | 22 | 48 | 48 |
| Nanoviridae | DNA | s | 36 | 28 | 17 | 37 | 40 |
| Partitiviridae | RNA | d | 36 | 42 | 35 | 60 | 58 |
| Closteroviridae | RNA | s | 37 | 32 | 20 | 46 | 48 |
| Baculoviridae | DNA | d | 41 | 16 | 10 | 38 | 33 |
| Caulimoviridae | DNA | d | 46 | 32 | 18 | 48 | 48 |
| Arteriviridae | RNA | s | 49 | 6 | 6 | 12 | 12 |
| Luteoviridae | RNA | s | 49 | 10 | 8 | 18 | 20 |
| Podoviridae | DNA | d | 60 | 34 | 30 | 66 | 66 |
| Rhabdoviridae | RNA | s | 60 | 24 | 18 | 40 | 40 |
| Tombusviridae | RNA | s | 61 | 31 | 24 | 60 | 54 |
| Myoviridae | DNA | d | 62 | 36 | 29 | 78 | 66 |
| Hepeviridae | RNA | s | 65 | 4 | 4 | 8 | 8 |
| Parvoviridae | DNA | s | 68 | 34 | 26 | 56 | 54 |
| Adenoviridae | DNA | d | 71 | 20 | 14 | 32 | 30 |
| Herpesviridae | DNA | d | 79 | 22 | 20 | 58 | 48 |
| Bromoviridae | RNA | s | 80 | 55 | 44 | 108 | 91 |
| Caliciviridae | RNA | s | 80 | 26 | 20 | 50 | 44 |
| Flexiviridae | RNA | s | 100 | 59 | 42 | 125 | 98 |
| Papillomaviridae | DNA | d | 100 | 44 | 21 | 103 | 97 |
| Arenaviridae | RNA | s | 103 | 38 | 21 | 93 | 80 |
| Microviridae | DNA | s | 105 | 10 | 6 | 14 | 12 |
| Togaviridae | RNA | s | 105 | 20 | 10 | 32 | 31 |
| Poxviridae | DNA | d | 133 | 16 | 6 | 22 | 20 |
| Paramyxoviridae | RNA | s | 159 | 36 | 26 | 60 | 56 |
| Siphoviridae | DNA | d | 162 | 69 | 45 | 145 | 130 |
| Potyviridae | RNA | s | 196 | 41 | 26 | 119 | 106 |
| Polydnaviridae | DNA | d | 230 | 181 | 80 | 331 | 333 |
| Coronaviridae | RNA | s | 237 | 13 | 10 | 24 | 24 |
| Circoviridae | DNA | s | 336 | 14 | 14 | 26 | 25 |
| Picornaviridae | RNA | s | 426 | 34 | 28 | 67 | 56 |
| Geminiviridae | DNA | s | 427 | 55 | 36 | 167 | 126 |
| Polyomaviridae | DNA | d | 499 | 20 | 10 | 28 | 24 |
| Flaviviridae | RNA | s | 522 | 34 | 26 | 81 | 68 |
| Reoviridae | RNA | d | 869 | 634 | 360 | >319 (58%)* | 866 |
| Hepadnaviridae | DNA | d | 975 | 6 | 6 | 8 | 12 |
| Bunyaviridae | RNA | s | 1010 | 207 | 125 | 449 | 326 |
| Retroviridae | RNA | s | 1348 | 64 | 44 | 164 | 124 |
| Orthomyxoviridae | RNA | s | 25237 | 236 | 145 | >242 (95%)* | 397 |

*Run did not complete in allotted time (100 hours). >319 (58%) indicates that with 319 primers, 58% of the target genomes were amplified.

Hypothetically, the worst case scenario to amplify a target set of N sequences would require 2N primers. MPP requires on average only 26%, 33%, 47% or 48% of this number for primers of length 10 nt without $T_m$ constraints, 10 nt with $T_m$ constraints, 17-18 nt, and 17-20 nt, respectively (averages across families for each column of Table 2). The most diverse families, in particular Reoviridae, Orthomyxoviridae (including all sequenced segments of influenza as well as other viruses in the family), Bunyaviridae, and Polydnaviridae, require so many primers that actually applying family-level amplification may well be infeasible. For these, more restricted target sets may be necessary, and possibly the incorporation of primers with degenerate or inosine bases. Some families with many genomes can be amplified with relatively few primers, such as Coronaviridae, Hepadnaviridae, Poxviridae, Togaviridae, Microviridae, and Polyomaviridae. All primer sequences are available in Appendix A.

Figure 9:
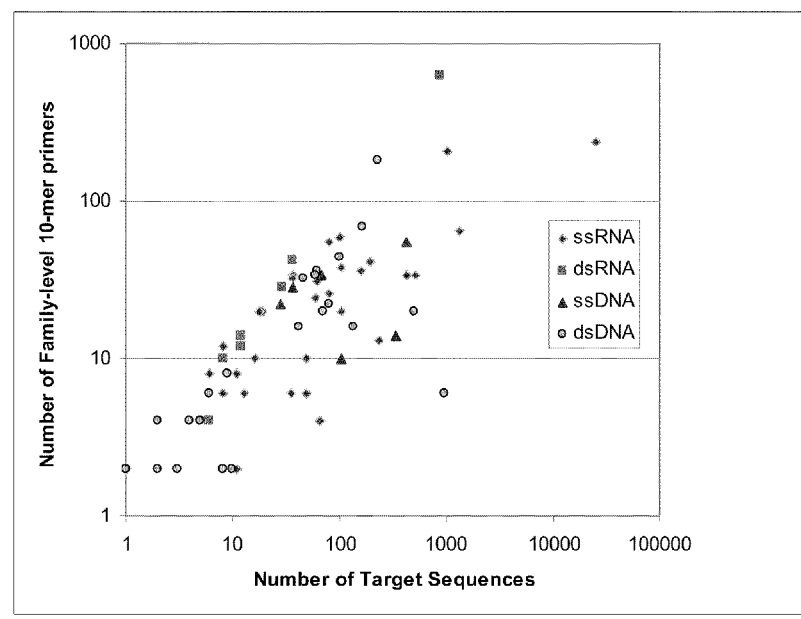
FIG. 9 shows a diagram plotting the number of primers required to amplify fragments from each complete genome or segment in a viral family versus the number of available sequences in that family. Primer numbers were for 10-mers, $T_m$ between 35-50° C., binned in groups of 20 primers/bin.

The size of the family-level primer set increases with the number of sequences in the family (FIG. 9, p=0.003, least squares fit). The number of primers in the set is not significantly affected by whether the genomes are RNA or DNA (p=0.08) or double or single-stranded (p=0.11, interaction term for DNA/RNA×ds/ss has p=0.07), although the plot indicates there is a trend for dsRNA genomes to require relatively more primers when controlling for the effect of the number of target sequences available.

Primer design with the software described above indicates that relatively few primers are required to amplify all sequenced genomes of HIV-1, FMDV, and Norwalk virus (Table 3).

TABLE 3

| Virus Species | Number of sequences | Number of 10-mers | Number of 17-18-mer primers in set | Longest conserved region from MSA (nt) |
|---|---|---|---|---|
| NA segment of Influenza A* | 6375 | 52 | 120 | 5 |
| HA segment of Influenza A* | 5440 | 73 | 153 | 1 |
| HIV-1 | 1175 | 6 | 16 | 0 |
| FMDV | 187 | 4 | 6 | 9 |
| Norwalk | 41 | 7 | 20 | 6 |

*For Influenza A HA and NA segments, all complete sequences, including lab strains, from all hosts, countries, and serotypes were downloaded from the NCBI Influenza Virus Resource database on Jan. 18, 2008.

Influenza A HA and NA segments demand large numbers of 10-mer or 17-18-mer primers, so one could break these into subgroups, possibly by serotype, as shown for several HA serotypes in Table 4.

TABLE 4

| Influenza A HA Serotype | Number of sequences | Number of 18-mer primers in set |
|---|---|---|
| H1 | 1080 | 24 |
| H2 | 108 | 8 |
| H3 | 1972 | 15 |
| H5 | 1325 | 16 |
| H7 | 256 | 8 |

Figure 10:
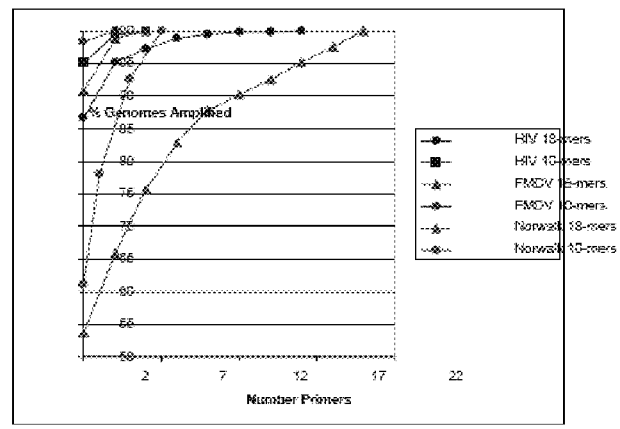
FIG. 10 shows a diagram plotting the percentage of genomes amplified versus the number of primers required, for primers of either 10-mers or 17-18-mers, for virus species HIV-1, FMDV, and Norwalk, according to an embodiment herein disclosed.
Figure 11:
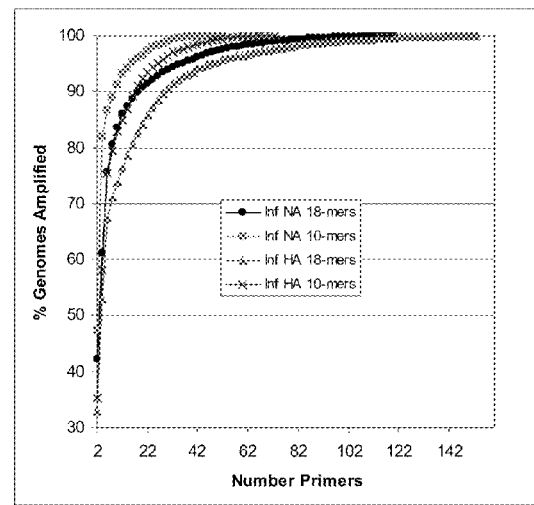
FIG. 11 shows a diagram plotting the percentage of genomes amplified versus the number of primers required, for primers of either 10-mers or 17-18-mers, for virus species Influenza A HA and NA segments, according to an embodiment herein disclosed.

The percentage of genomes amplified versus the number of primers used, for primers of either 10-mers or 17-18-mers, is shown in FIGS. 10 and 11. These plots show that a large fraction of targets are amplified with only 2 primers, and the addition of subsequent primers shows diminishing returns in amplifying fewer, more divergent targets not detected by the initial, more conserved, primer pair.

The more traditional method of attempting to find primers from a multiple sequence alignment would be problematic, probably requiring manually designed primer multiplexes or highly degenerate primers. For HIV-1, for example, there is not a single position with 100% conservation across all sequenced isolates. Dropping the required conservation down to 95% (58 of the 1175 genomes could disagree with a consensus base at any position), there are 3 conserved regions of at least 18 bases, with positions relative to the consensus: ACAGGAGCAGATGATACAGTA (SEQ ID NO: 11,335) starting at position 3665; TATGGAAAACAGATGGCAGG (SEQ ID NO: 11,336) starting at 7347; and CTATGGCAGGAAGAAGCG (SEQ ID NO: 11,337) starting at 9071. These regions are too far apart to be used as primers for most polymerases used in diagnostic PCR protocols, where amplicons must typically be less than 300 bases long for efficient amplification. A recently published study [ref. 30] selected primers from the 5' LTR U5 end to the Gag-Pol start (5'-TAGCAGTGGCGCCCGA-3' (SEQ ID NO: 11,338) and 5'-TCTCTCTCCTTCTAGCCTCCGC-3' (SEQ ID NO: 11,339), but a comparison against available genomic data indicates that 487 of the 1175 genomes (41%) do not contain a sequence match for this primer pair, so may fail to be amplified.

For Influenza A segment HA, the size of the longest conserved region from the 95% consensus is only 5 bases, and for segment NA, only 6 bases, insufficient for even a single primer. For FMDV and Norwalk virus, the longest 100% conserved regions are 9 and 6 bases, respectively, too short for a primer. Thus, for highly diverse and large targets such as these, one option for primer design is careful manual selection by an expert in multiplex and/or degenerate PCR. Applicants tried several freely available tools, and found that they had difficulty scaling for large target sets (see below). MPP software makes it straightforward for a non-expert to determine a multiplex-compatible set of conserved primers, even for enormous and heterogeneous target sets that cannot be aligned.

For comparison, Applicants considered other software options for designing primers for these heterogeneous viruses. Applicants tried Primaclade® [ref. 34], but the web server timed out for Norwalk and FMDV alignments. The link to the MuPlex [ref. 40] server was not functional, and in any case the file size limit of 500 Kb would have been exceeded by all but the Norwalk data set. The PDA-MS/UniQ software [ref. 35] was not available for download or on a public web server. CODEHOP [ref. 41] requires protein alignment as input so is not appropriate for whole-genome (nucleotide) alignments.

SCPrimer [ref. 36] did generate a number of degenerate primer candidates from the multiple sequence alignment, requiring the user to manually select a combination of forward and reverse groups from a set of options. Applicants ran SCPrimer using length, $T_m$, etc. settings mirroring or more lenient than those Applicants used for Table 3 ($T_m$=55-65° C., GC %=20-80%, length 17-25 bp, 100% coverage, product size 80-620 bp, allowed $T_m$ difference 10° C., others left as defaults). HYDEN [ref. 38] also generated degenerate candidates from the multiple sequence alignment, although it does not check $T_m$ and the length is limited to a single value rather than a range (Applicants set it at 18 rather than 17 because of the lack of $T_m$ control, and allowed 0 mismatches). The SCPrimer option requiring the fewest total primers for the Norwalk set required 18 primers, 4 of which had either 2-fold or 4-fold degeneracy so the actual number of priming sequences would be 26, compared to a total of 20 non-degenerate primers predicted by MPP (Supplementary information). HYDEN generated 4 degenerate primers covering only 34 of 41 sequences, each with 3- or 4-fold degeneracy for Norwalk, which translates to 15 priming sequences in the reaction. Small degenerate priming sets (e.g. 4 primers in this case) are less expensive to purchase, but because of dilution effects from the many sequence combinations actually present (15 priming sequences in the PCR), sensitivity may be reduced compared to nondegenerate priming.

One would need to manually find primers to amplify the remaining seven sequences. For FMDV, SCPrimer generated a number of candidates, and manual inspection identified that the best of those primer combinations would require 6 primers, one of which had 2-fold and another had 3-fold degeneracy, totalling 9 actual priming sequences in a reaction (Appendix A). This compares with 2 primers each with 4-fold degeneracy using HYDEN (8 priming sequences in a reaction), to amplify 98% (183 of 187) targets, and 6 non-degenerate multiplex compatible primers for FMDV using MPP.

Example 6

Calculating Highly Conserved, Multiplexed Primer Sets

Here, Applicants outline a greedy algorithm used to calculate conserved sets of multiplexed primers to amplify fragments from each member of a target set of sequences. An exemplary source code is enclosed herewith as Appendix E incorporated herein by reference. First, Applicants enumerate all candidate oligos fitting requirements for length, $T_m$ (see Table 5), and lack of hairpin formation (minimum hairpin $\Delta G$ was −5 kcal/mol).

TABLE 5

$T_m$ (° C.) settings used in predicting universal primer sets

| | Length | | | | | | | | | | | | |
|---|---|---|---|---|---|---|---|---|---|---|---|---|---|
| | 6 | 7 | 8 | 9 | 10 | 11 | 12 | 13 | 14 | 15 | 16 | 17 | 18 |
| $T_m$ min | 10 | 25 | 30 | 35 | 35 | 35 | 35 | 40 | 45 | 50 | 50 | 50 | 50 |
| $T_m$ max | 35 | 40 | 45 | 50 | 50 | 50 | 50 | 55 | 60 | 65 | 70 | 70 | 70 |

Applicants rank pairs of these by the number of targets in which that pair occurs within a distance d of one another, and the most frequent pair is selected as primers.

The process is repeated for the remaining targets that would not have an amplicon from the first pair, with the added consideration that new oligos selected be predicted not to form dimers with other primers already in the bin, based on nearest neighbor thermodynamic predictions [ref. 16], allowing a primer dimer minimum $\Delta G$ of −7 kcal/mol. Primers are added to a bin until that bin contains 20 primers, at which point a new bin is begun, following the same process. Binning primers in groups of 20 avoids exclusion of the most highly conserved oligos because of primer dimer free energy constraints. In other embodiments, other bin sizes may be desired, and primer sets can be built by specifying more or fewer primers per bin.

Figure 7:
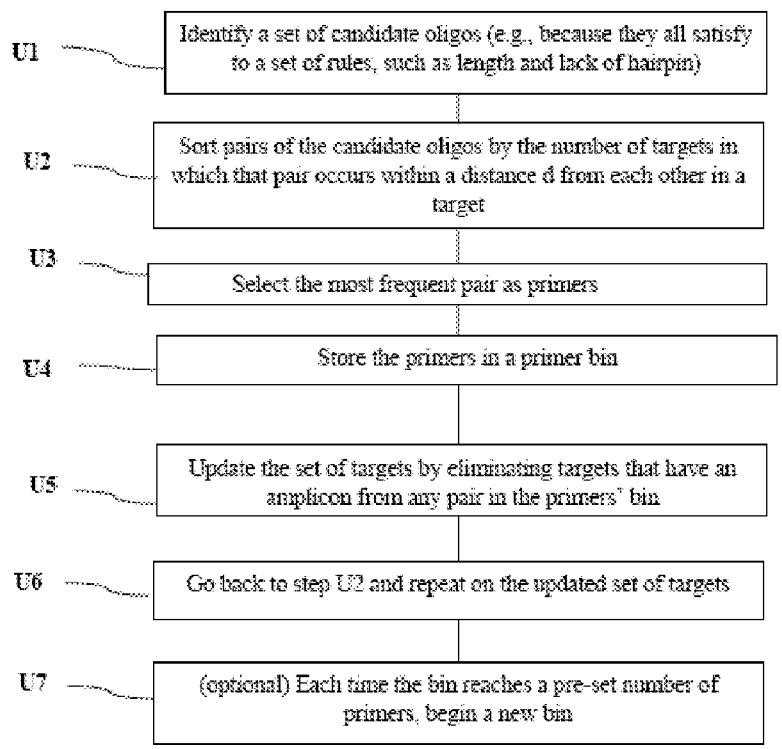
FIG. 7 shows a third exemplary algorithm to identify probe polynucleotides according to an embodiment herein disclosed.

An embodiment of the present disclosure on which Example 6 is based is shown in the flowchart of FIG. 7, which shows steps U1-U7 for performing a method to identify primers suitable for detecting target microorganisms.

The universal set of primers is the set of selected primers to amplify all genomes in the target set. The primers within a bin should be multiplexed into a single PCR reaction, but each bin run separately. Applicants calculated universal primers of length 5-18, and analyzed how primer length affects the number of primers in the universal set. The allowable range for distance d used here was between 80 and 620 bases, as this is reasonable for electrophoretic discrimination of bands or sequencing.

Figure 12:
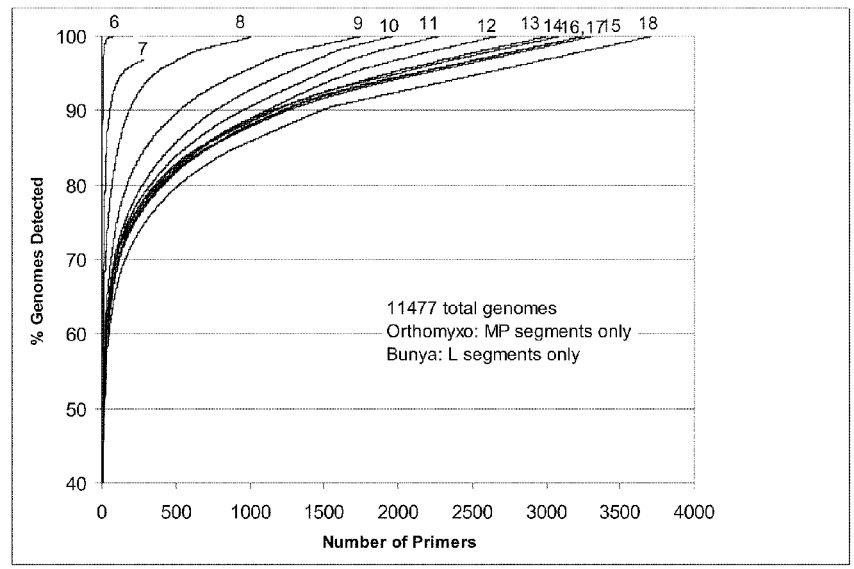
FIG. 12 shows a diagram plotting the percent of viral genomes detected vs. number of primers required, for primers of different sizes based on all available viral genomes, using sequence data as of Apr. 25, 2007.

The number of primers in a universal viral set such that all viral genomes generate at least one amplicon is shown in FIG. 12. For segmented viruses, primers were designed so that an amplicon from each segment should be amplified, except for the case of Orthomyxovirida, in which primers were designed to only ensure amplification of MP segments, and Bunyaviridae, in which primers were designed to only ensure amplicons from L segments. With 10-mer primers, 1974 primers are required to detect all viral genomes, but this number drops by over half, down to 764 primers, if it is sufficient to detect only 90% of viral targets. For 9-mers, 1754 and 525 primers are required to detect 100% or 90%, respectively. Using longer primers such as 15-mers requires 3318 primers for 100% or 1246 primers for 90%. Requiring 7-mers with $25°\le T_m\le 40°$ C., it is not possible to amplify all target genomes, since many do not contain pairs of 7-mers in the required $T_m$ range within a PCR-amplifiable distance of one another. $T_m$ constraints demand larger universal primer sets (FIG. 13) since some highly conserved primers may be eliminated because of $T_m$'s outside the allowable range.

Figure 13:
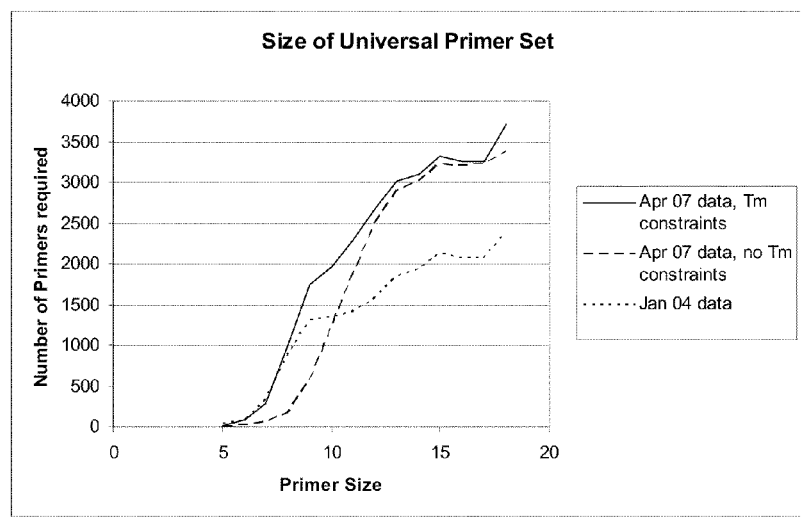
FIG. 13 shows a diagram plotting the number of primers in the universal set for all viruses, as a function of primer size, based on sequence data available April 2007 and imposing $T_m$ constraints in primer selection, without $T_m$ or GC % constraints, and based on January 2004 sequence data with $T_m$ constraints. For primer size of 5 with $T_m$ constraints, a constraint of $T_m>0$ was used, delivering primers with GC % of 80-100%.

This is particularly true for shorter primers, since short primers more often fall below the allowable $T_m$ range. In FIG. 13, the solid and dotted curves with $T_m$ constraints are jagged because of the arbitrary increment in allowable $T_m$ range that was specified for primers of different lengths. Removing any primer $T_m$ or GC % constraints, the number of primers in a universal set for all viruses can drop by up to 83%: for 8-mer primers, the size of the universal set is 1000 primers or 172 primers for runs with $T_m$ constraints versus without, respectively. The magnitude of this advantage is greater for shorter primers, which have low $T_m$'s to begin with. Protocols for specific PCR amplification using short, low-$T_m$ primers could be advantageous.

If primers are not separated into reaction bins of 20 primers/bin, and instead all mixed in a single reaction, using 10-mers, Applicants predict that 1008 primers would be required to ensure amplification of at least one fragment 80-620 bp from every viral genome. This is a savings of almost 50% of the total number of primers required, compared to binning the reactions. To ensure that this computation would complete, Applicants relaxed the primer dimer minimum $\Delta G$ to −11 (from −7 kcal/mol for the binned runs), and the calculation required 776 hrs.

Another alternative (to removing $T_m$ constraints or combining primers in a single, unbinned reaction) for reducing the number of primers is to allow primer length variation while maintaining $T_m$ within a specified range, although this requires substantially more memory to calculate. There was not enough memory to compute a universal set allowing primers of lengths between 12-15 bases on a 32 MB node. A universal set of 12-14-mers with $40°\le T_m\le 55°$ C. requires 2805 primers grouped into 140 reaction bins, a savings of ~200 primers compared to 13-mers alone with the same $T_m$ range (3015 primers). Similarly, a universal viral set of primers ranging in size from 9-11-mers gives a savings of ~200 primers compared to fixed length primers of size 9-mers with the same $T_m$ range ($T_m$ of 35-50° C., 1561 versus 1754 primers).

It is predicted that ~2000 primers of length 10 would be required to amplify fragments from all currently sequenced viruses, or ~3700 primers of length 18. With primers longer than 10 bases, however, it is likely that newly emerging, unsequenced viruses would go undetected Example 7

Genome Targets Used in Calculations

Viral Genomes

Our target set for the calculation of Example 6 was the set of all viral genomes and segments, using only the MP segment from Orthomyxoviridae and the L segment of Bunyaviridae, in order to limit the overrepresentation of these families, totaling 11,477 sequences on Apr. 25, 2007, when Applicants compiled the data. Including the MP segment and L segment of Orthomyxoviridae and Bunyaviridae, respectively, would have resulted in a total of 34,494 sequences, illustrating the large representation of those families in viral sequence databases. Draft sequences with multiple contigs were merged into a single sequence entry, with contigs separated by 1000 N's, a stretch sufficiently long (>d) so that primer pairs would not be designed to fall on different contigs.

Each calculation was performed on a single AMD Opteron 2.4 GHz processor with 16-32 GB of RAM. The total compute hours to generate the results described here was over 11,000 cpu-hours, taking advantage of high performance computing facilities at Lawrence Livermore National Laboratory.

Thus, viruses pose a unique challenge compared to bacteria, where 16s rRNA primers are highly conserved across the bacterial kingdom. Random amplification and sequencing of a few 100 nt fragments from an unknown virus is an alternative approach that is predicted to successfully characterize newly emerged viruses. Targeted amplification with a single or few (<10) pentamer or hexamer priming sequences is another possible strategy for viral amplification for detection/characterization that may work if the specific pentamers or hexamers are chosen wisely.

Example 8

Figure 15:
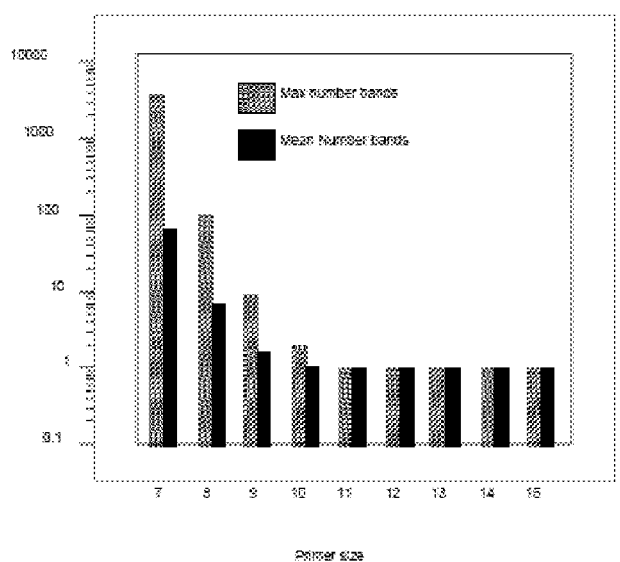
FIG. 15 shows a block diagram illustrating the maximum number of bands and mean number of bands per genome in a bin as a function of primer size, predicted using the universal primer sets for all viral genomes and segments as indicated in FIG. 12.

Virus Detection Through Viral Genome Identification from Universal Viral Primer Sets To deconvolute and characterize the PCR products, there must not be too many different amplicons per genome if the backend is via fragment length distributions, mass spectrometry, or sequencing (although microarray hybridization might be more flexible in this regard). One could envision that 1-10 amplicons per genome would allow adequate discrimination of genomes. Universal viral primer sets of size 7 or 8-mer primers result in 10's to 1000's of different amplicons per genome per bin, since multiple primers bind (some more than once) to each genome (FIG. 15). 9-mers generate approximately 1-10 amplicons for most genomes, and 10-15-mers usually generate only a single band. Using unbinned 10-mer primers run all within a single reaction (the set of 1008 primers described above), the mean and maximum number of amplicons per genome are 13.2 and 948, respectively, compared to a mean of 1 and maximum of 2.9 amplicons per genome using the 10-mers binned into groups of 20 primers/bin. So by using a larger multiplexed reaction, not only might primer multiplexing be more difficult, but also deconvoluting the products might be more challenging.

Example 9

Family Identification by Sequencing Fragments Amplified Using a Universal Primer Set The products of amplification using a universal viral primer set could be sequenced, so the question arises of whether the amplified fragments can provide family-level characterization of unknown, newly emerged viruses.

Figures 17, 18:
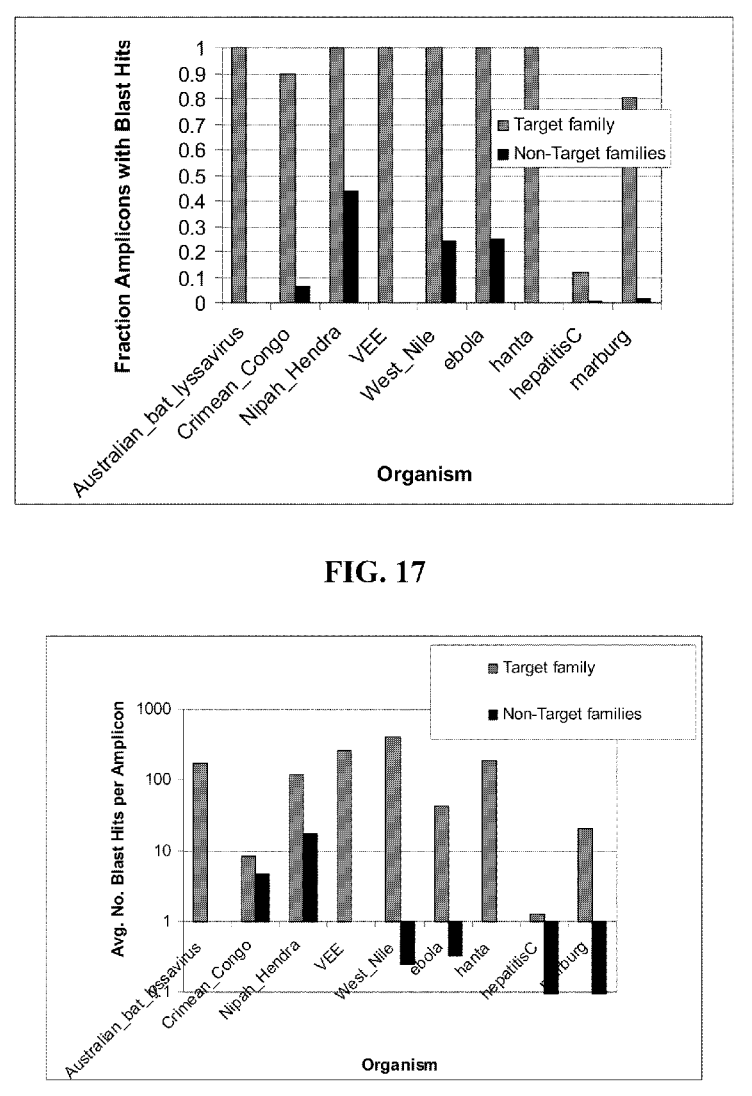

Applicants extracted the sequence of the amplicons that should be generated using specific amplification with the universal 10-mer set and BLASTed those amplicon sequences against either other species in the same target family or viruses in other families (FIGS. 17 and 18).

This shows that on average 87% of the amplicons have BLAST hits in the correct family, with an average of 135 hits per amplicon. In contrast, only 11% of amplicons have BLAST hits in other, non-target families, with an average of 2.5 BLAST hits per amplicon Example 10

Identification of Unknown Viruses

To determine the likelihood of detecting unknown/unsequenced viruses, Applicants performed the following simulations. The 29 most recently emerged species of viruses [ref. 14, 28] and their very similar subsequently discovered near neighbors (Table 6) were excluded from the target set of genomes, leaving 9741 sequences.

TABLE 6

Reference sequences of newly emerged viruses

Arenaviridae ref|NC_005077, NC_005082|Guanarito virus

Arenaviridae ref|NC_004296, NC_004297|Lassa virus

Arenaviridae ref|NC_006572, NC_006573|Mopeia Lassa reassortant 29

Bunyaviridae ref|NC_005215, NC_005216, NC_OO5217|Sin Nombre virus

Bunyaviridae ref|NC_005226, NC_005227, NC_005228|Tula virus, complete

Bunyaviridae ref|NC_005300, NC_005301, NC_005302|Crimean-Congo hemorrhagic fever virus Bunyaviridae ref|NC_003466, NC_003467, NC_003468|Andes virus Bunyaviridae ref|NC_002043, NC_002044, NC_002045|Rift Valley fever virus Coronaviridae ref|NC_004718.3|gnl|NCBI_GENOMES|17014|gi|30271926|SARS coronavirus Dicistroviridae ref|NC_003005.1|gnl|NCBI_GENOMES|15715|gi|14780876|Taura syndrome virus Filoviridae ref|NC_006432.1|gnl|NCBI_GENOMES|18041|gi|55770807|Sudan ebolavirus Filoviridae ref|NC_002549.1|gnl|NCBI_GENOMES|15507|gi|10313991|Zaire ebolavirus Filoviridae ref|NC_001608.2|gnl|NCBI_GENOMES|10467|gi|13489275 Lake Victoria marburgvirus Filoviridae ref|NC_004161.1|gnl|NCBI_GENOMES|16606|gi|22789222 Reston Ebola virus Flaviviridae ref|NC_001563.2|gnl|NCBI_GENOMES|10411|gi|11528013 West Nile virus Flaviviridae ref|NC_001437.1|gnl|NCBI_GENOMES|10160|gi|9626460|Japanese encephalitis virus TABLE 6-continued Reference sequences of newly emerged viruses

```
Flaviviridae ref|NC_004102.1|gnl|NCBI_GENOMES|16556|gi|22129792|Hepatitis C virus Hepeviridae ref|NC_001434.1|gnl|NCBI_GENOMES|10157|gi|9626440|Hepatitis E virus Paramyxoviridae ref|NC_002728.1|gnl|NCBI_GENOMES|15627|gi|13559808|Nipah virus Paramyxoviridae ref|NC_007620.1|gnl|NCBI_GENOMES|19015|gi|82712717|Menangle virus Paramyxoviridae ref|NC_001906.2|gnl|NCBI_GENOMES|13716|gi|29468603|Hendra virus Paramyxoviridae ref|NC_004074.1|gnl|NCBI_GENOMES|16538|gi|22003842|Tioman virus Retroviridae gi|1906382|gb|K03455.1|HIVHXB2CG Human immunodeficiency virus type 1 (HXB2),
complete genome; HIV1/HTLV-III/LAV Retroviridae ref|NC_00 1870.1|gi|9629914|gnl|NCBI_GENOMES|13303|Simian-Human immunodeficiency
virus Retroviridae ref|NC_001722.1|gnl|NCBI_GENOMES|10902|gi|9628880|Human immunodeficiency virus Retroviridae ref|NC_001802.1|gnl|NCBI_GENOMES|12171|gi|9629357|Human immunodeficiency virus Rhabdoviridae ref|NC_003243.1|gnl|NCBI_GENOMES|15865|gi|17158068|Australian bat lyssavirus Togaviridae ref|NC_001786.1|gnl|NCBI_GENOMES|11742|gi|9629246|Barmah Forest virus Togaviridae ref|NC_001449.1|gnl|NCBI_GENOMES|10176|gi|9626526|Venezuelan equine encephalitis
virus
```

Then sets of universal primers of lengths 7-15 were generated for this subset of sequence data that excluded the newly emerged viruses. These primers were then compared to each of the reference sequences of the newly emerged species, and the fraction that would have been detected was calculated (FIG. 16).

For 10 newly emerged viruses, the amplicon sequences predicted using the conserved universal set of 10-mer primers (as calculated for FIG. 12) were BLASTed against other species from the same family, and also against sequences from other families. The fraction of amplicons with BLAST hits in the correct target family was compared to the fraction with hits to incorrect, non-target families (FIG. 13). This estimates the ability of the conserved universal 10-mer primer set to correctly characterize newly emerging viruses as to family.

Figure 16:
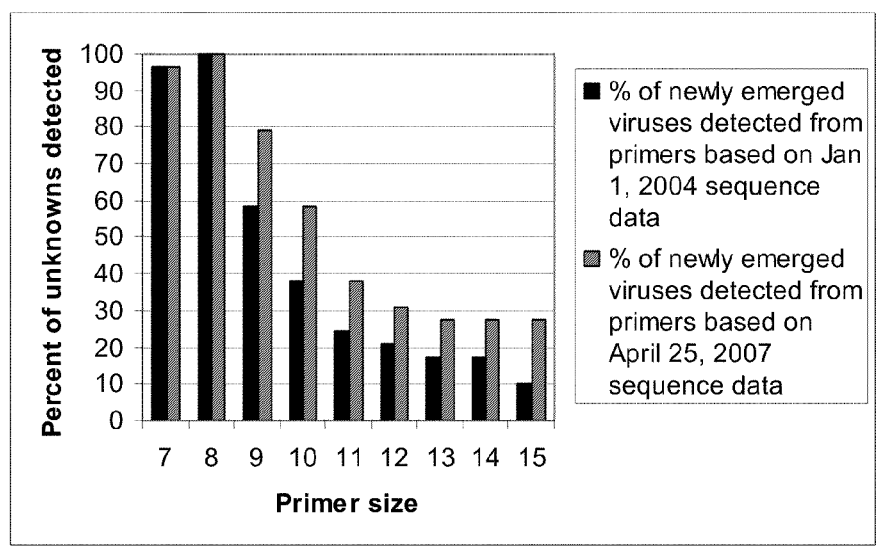
FIG. 16 shows a block diagram illustrating the percent of newly emerged ("unknown" viruses) that would have been detected based on sequence data available as of Jan. 1, 2004 or Apr. 25, 2007, as a function of primer length.

The ability to detect/discover uncharacterized or newly emerged viruses using viral universal primer sets depends strongly on primer size (FIG. 16). With 7 to 9-mers, Applicants' simulations indicate that the majority of newly emerged viruses would be detected, which in this case means that an amplicon should be generated. With 10-mers, more than half would have been detected. With primers longer than 10 bases, however, our simulations indicate that it is more likely that these newly emerged viruses would not have been detected. The amount of sequence data used to generate the universal primer sets also plays a role, such that with 9-10-mers, about 20% more newly emerged viruses could be detected (in the absence of sequence information for those unknowns and their subsequently discovered near neighbors) using primer sets generated in 2007 than in 2004.

Example 11

Effect of Increasing Availability of Sequence Data on Universal Primer Sets

Applicants evaluated how the growth of sequence availability could affect the size of the universal set, as well as our ability to detect unknown/unsequenced viruses, by compiling all viral genomes and segments available as of Jan. 1, 2004, totaling 9965 sequences. It was not necessary to exclude any Orthomyxoviridae or Bunyaviridae segments, because these sequences were not so deeply sequenced at that time.

Figure 14:
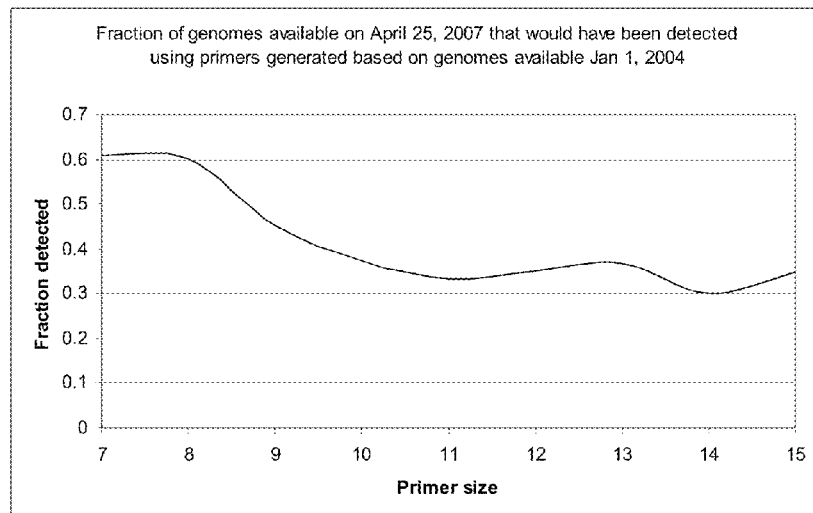
FIG. 14 shows a diagram plotting the fraction of viral genomes available on Apr. 25, 2007 that would have been detected using primer sets developed based on the sequence data available on Jan. 1, 2004.

First Applicants generated universal primer sets using all the data (FIG. 12). Applicants then determined how much of the 2007 sequence data would have been detectable using the 2004 primer sets (FIG. 14). In addition, Applicants excluded the newly emerged species as described above, generated universal sets, and determined how many of the newly emerged sequences Applicants would have been able to detect in January 2004 if Applicants had not had their sequences for designing the universal primer sets (FIG. 16).

The increase in sequence data between 2004 and 2007 requires approximately 700 more 10-mer primers to amplify all sequenced viruses in 2007 compared to 2004 (FIG. 13). While the increase in the number of sequences used between the two dates was only ~15%, the number of primers required increased by 48%, illustrating the substantial increase in diversity represented by the additional sequence data. Using universal primer sets generated using the 2004 sequence data, comparison against the 2007 sequence data indicate that only ~35% of the genomes sequenced in 2007 would have been detected using a set of 10 to 15-mer primers (FIG. 14). Shorter primers increase this fraction to over 60%, due to the higher likelihood of occurrence and conservation of shorter oligos.

Example 12

Random Amplification and Sequencing

An alternative strategy to specific amplification using universal primers is to perform amplification and sequencing of a few, randomly chosen fragments. To determine whether the sequences of randomly selected fragments of a specified length are likely to provide correct family classification of an unknown virus, simulations were performed by randomly selecting 10 fragments per length from each available genome of 10 newly emerged species (Australian bat lyssavirus, Crimean Congo hemorrhagic fever, Nipah, Hendra, Venezuelan equine encephalitis, West Nile, Ebola, Hanta, hepatitis C, and Marburg viruses), totalling 7250 fragments per length.

Each fragment was BLASTed against viruses in other families (non-target families), and also against viruses in the same family other than the species from which the fragments were derived. For Nipah and Hendra, since they are genetically so similar, both were excluded from the target family for BLASTing either of their fragments (i.e. they were treated as a single species).

Using tblastx, a positive BLAST hit required an e-value no more than 0.001 and a hit length of at least 17 amino acids (at least half the length of a 100 nt fragment, when translated to 33 amino acids). Results are plotted in FIGS. 19 and 20. To correct for disparities in the number of genomes per species, the average number of fragments with BLAST hits to target or non-target families was calculated for each species, and an overall mean h was calculated per fragment length from the mean values of all species.

Figure 20:
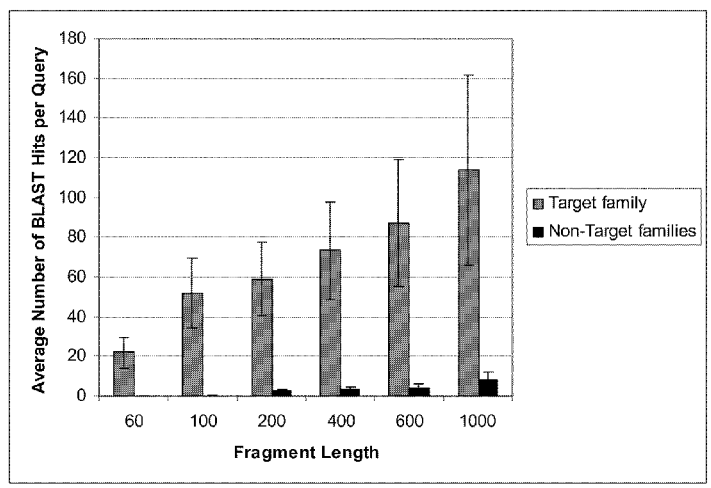
FIG. 20 shows a block diagram illustrating fragments of the lengths indicated, randomly chosen from the genomes of 9 newly emerged virus species and BLASTed against other viruses in the same (target) family or viruses in other (non-target) families are plotted against the average number of BLAST hits per fragment (+/− standard errors).
Figure 21:
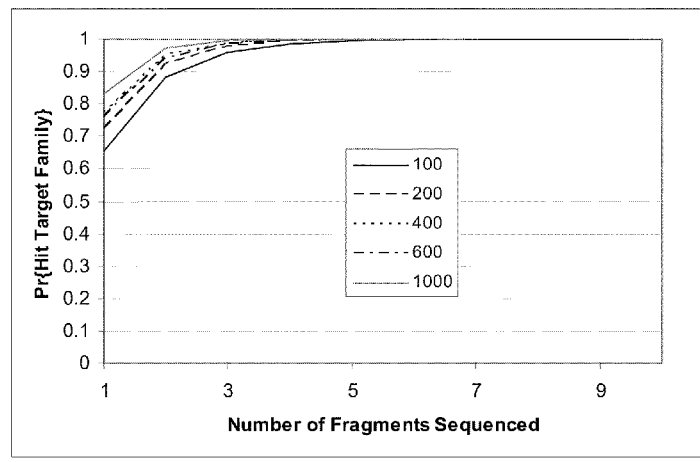
FIG. 21 shows a diagram illustrating the probability that at least one fragment has BLAST hits to the correct target family, calculated as indicated in the text.
Figure 22:
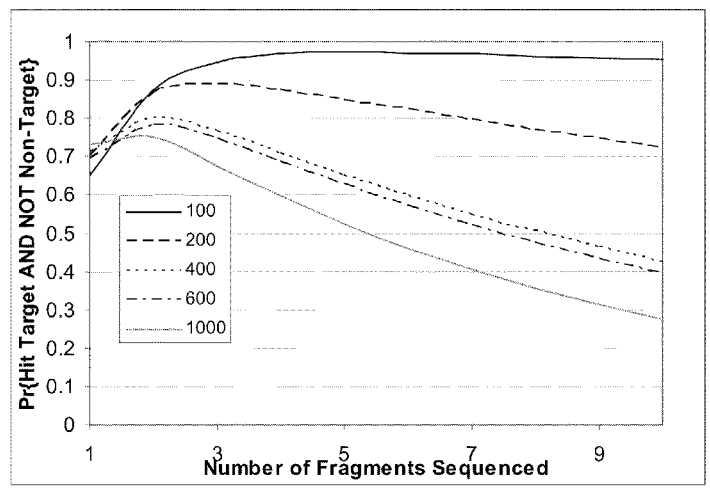
FIG. 22 shows a diagram illustrating the probability that at least one fragment has BLAST hits to the correct family and no fragments have BLAST hits to the incorrect family, calculated as indicated in the text.

The average number of BLAST hits per fragment is another measure of similarity (FIG. 20). The probability that an "unknown" has at least one BLAST hit in the correct family as a function of the number n of fragments sequenced and hits $h_{target}$ is $1-(1-h)^n$, shown in FIG. 21. The probability of at least one BLAST hit in the correct family and no BLAST hits in the incorrect family is $(1-(1-h_{target})^n)(1-h_{non-target})^n$, in FIG. 22. In FIGS. 21 and 22 sequencing several 100 bp fragments is more informative as to correct viral family of an unknown than sequencing a single 1000 bp fragment.

Figure 19:
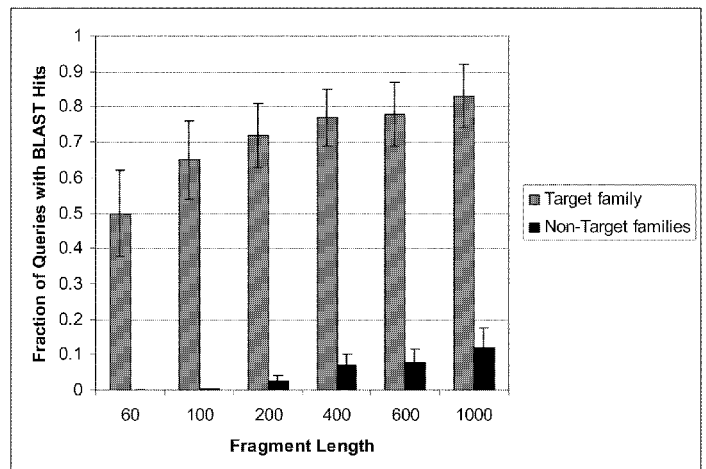
FIG. 19 shows a block diagram illustrating fragments of the lengths indicated, randomly chosen from the genomes of 9 newly emerged virus species and BLASTed against other viruses in the same (target) family or viruses in other (non-target) families are plotted against the fraction of fragments (queries) with BLAST hits.

Another strategy for viral characterization is random rather than specific amplification, followed by sequencing a small number of amplified fragments. Applicants did these simulations, using randomly chosen fragments of a given length instead of fragments amplified by a universal primer set (FIGS. 19 and 20). As with specifically amplified fragments, the chance of sequence similarity to other species in the correct family far exceeds that to viruses in other families. The percentage of specifically amplified fragments with BLAST hits exceeds that for randomly amplified fragments because the conserved primers target areas of higher sequence conservation than randomly selected fragments.

If viral characterization is to be done by sequencing randomly chosen fragments, the question arises of whether it is better to sequence more, shorter fragments or fewer, longer fragments. The fraction of fragments and number of hits per fragment from a newly emerged virus to known viruses increase with fragment length, although the increase shows diminishing returns for lengths over 100 bases. Thus, simulations indicate that 3 fragments of 100 bp would have a higher probability of classifying a virus as to the correct family, since the chance of BLAST hits to target family and not to non-target families is higher for 3 100-mer fragments than for other scenarios (FIGS. 21 and 22).

Example 13

Targeted Amplification with a Conserved 5-6-mer

A third strategy to amplify a limited number of fragments for sequencing from any virus might be to select a single (or few) very short, highly conserved sequence (e.g. 6 bases) with which to prime. Ideally, a single hexamer could be found that should amplify a small number of fragments per genome for every viral genome.

Figure 23:
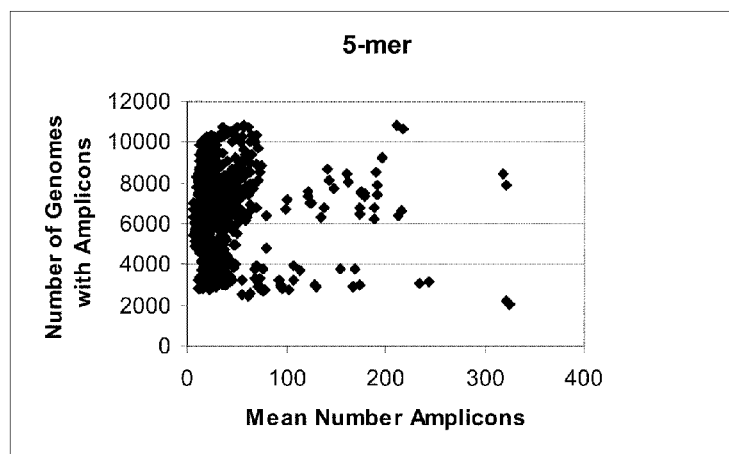
FIG. 23 shows a diagram illustrating viral discovery according to an embodiment herein disclosed performed by amplifying with a single pentamer followed by sequencing the products.
Figure 24:
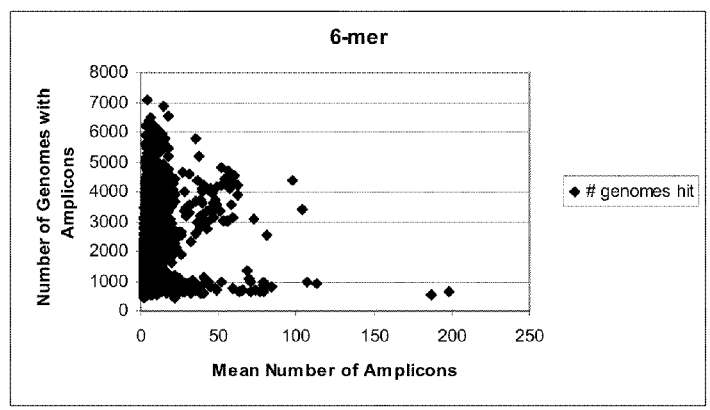
FIG. 24 shows a diagram illustrating viral discovery according to an embodiment herein disclosed performed by amplifying with a single hexamer, followed by sequencing the products.

Applicants enumerated all 4096 hexamers and 1024 pentamers, and calculated all the amplicons that would be produced between length 70-1000 bp if primed by a single penta- or hexamer, for each of the 11,477 viral genomes and segments (including only the MP segment from Orthomyxoviridae and the L segment of Bunyaviridae, as described above). The range of 70-1000 bp limits amplicons to lengths feasible for PCR, electrophoresis, and sequencing. The number of genomes with at least one amplicon was determined, as well as the maximum and mean number of amplicons per genome (with mean calculated based on those with at least one), in order to identify the most promising short oligos to use for universal priming of viral genomes (FIGS. 23 and 24).

The third strategy Applicants investigated using bioinformatics was that of using a single pentamer or hexamer 3' anchor sequence to amplify fragments from the maximum number of viral genomes, and ideally to amplify only a small number of fragments per genome for easy analysis by, for example, length, base composition, or sequence. As indicated in FIGS. 23 and 24, oligos exist that approach this goal (oligos giving points in the upper left corners of the plots), but none are perfect, so that either one risks missing some genomes and/or amplifying so many fragments that it would be difficult to decipher the results. The best sequences are shown in Table 7, and the complete list is available upon request from the Applicants.

| Sequence | SEQ ID NO | # genomes amplified | Mean # amplicons per genome | Max # amplicons per genome |
|---|---|---|---|---|
| AAATG | 11,340 | 10798 | 57 | 3523 |
| CAAGA | 11,341 | 10349 | 24 | 1421 |
| AATCC | 11,342 | 10250 | 20 | 1238 |
| TCAGG | 11,343 | 10065 | 15 | 617 |
| AGACC | 11,344 | 9902 | 13 | 560 |
| CACTT | 11,345 | 9892 | 16 | 1245 |
| TCCATG | 11,346 | 7066 | 5 | 68 |
| CCAAAA | 11,347 | 6477 | 6 | 116 |
| CATGGA | 11,348 | 6356 | 5 | 73 |
| CAAAGC | 11,349 | 6217 | 3 | 57 |
| CACTTG | 11,350 | 5894 | 3 | 123 |
| TCCATG and CAAAGC | 11,346 and 11,349 | 9449 | 8 | 134 |
| All 5 hexamers | 11,346-11,349 | 10703 | 40 | 1275 |

The pentamer AAATG (SEQ ID NO: 11,340) amplifies 10,798 of the 11,477 viral genomes, but the mean and maximum number of amplicons per genome is somewhat high, 57 and 3,523, respectively. Instead, the pentamer AGACC (SEQ ID NO: 11,344), which amplifies 9902 genomes with an average of 13 amplicons per genome and a maximum of 560 amplicons per genome, might enable easier amplicon characterization. The best hexamer amplifies only 7066 genomes, but only produces on average 4.6 bands/genome, and never more than 68. Combining two of the best hexamers, TCCATG (SEQ ID NO: 11,346) and CAAAGC (SEQ ID NO: 11,349) in a single reaction, generates amplicons in 9449 genomes, with an average and maximum of 8 and 134 amplicons per genome, respectively. Combining the 5 hexamers in Table 3 in a single reaction mix would amplify 10,703 genomes, with an average and maximum of 40 and 1275 amplicons per genome, which comes closer to our goal of maximizing genomes with amplicons while minimizing amplicons per genome, than using the single best pentamer.

The genomes that typically give many amplicons are long, for example, from the families Herpesviridae, Poxviridae, and Phycodnaviridae. One might amplify a sample in two separate reactions, one in which a more common penta- or hexamer were used to ensure amplification from all viruses, and the other with a less common oligo that would produce intelligible amplicon distributions even for long genomes. The 5-mer oligos used as 3' anchor sequences by Nanda for viral detection [ref. 17], TTCTG (SEQ ID NO: 11,351) and TGTGG (SEQ ID NO: 11,352), are predicted to amplify 9,051 and 7415 of the total 11,477 viral genomes, respectively. The (mean, maximum) number of amplicons per genome for TTCTG (SEQ ID NO: 11,351) and TGTGG (SEQ ID NO: 11,352) are predicted to be (29, 2847) and (23, 826), respectively.

Example 14

Targeted Amplification with a Conserved 7-mer to 30-mer

Universal primer sets consisting of short (7-30 base pair) nucleic acid strands has been created that can be used to amplify sequences of target viral DNA/RNA. These primer sets were designed to amplify specific nucleic acid sequences of all viral complete genomes sequenced to date, as well primer sets designed separately for various sub-groupings of the viruses, including for each of the vertebrate-infecting viral families. There are currently 28 known virus families that infect vertebrates. Fixing primer size at 10 bases (10-mer), requires between 2 and >700 primers in family-level universal sets (Table 8). The number of primers in a family's set increases with the number of available genomes for that family, as well as the diversity of the family, so Applicants anticipate that as new genomic sequences become available Applicants will need to update the universal primer sets identified so far. The sequences for representative sets of these primers are given in the enclosed Appendix A which makes part of the present specification and is herein incorporated by reference in its entirety.

TABLE 8

| | Family | number of genomes (or segments) | Number of primers, 10-15-mers[1] | Number of primers, 10-mers[2] | Maximum number of amplicons[3] | Mean number of amplicons[4] |
|---|---|---|---|---|---|---|
| 1 | Adenoviridae | 71 | 37 | 34 | 40 | 9.4 |
| 2 | Arenaviridae | 115 | 101 | 72 | 20 | 5.3 |
| 3 | Arteriviridae | 36 | 10 | 10 | 2 | 1.2 |
| 4 | Asfarviridae | 8 | 2 | 3 | 1 | 1.0 |
| 5 | Astroviridae | 14 | 13 | 12 | 4 | 2.1 |
| 6 | Birnaviridae | 12 | 18 | 16 | 2 | 1.2 |
| 7 | Bornaviridae | 9 | 2 | 2 | 1 | 1.0 |
| 8 | Bunyaviridae | 1004 | 144 | 402 | 25 | 5.5 |
| 9 | Caliciviridae | 70 | 53 | 43 | 9 | 2.8 |
| 10 | Circoviridae | 298 | 25 | 20 | 5 | 3.0 |
| 11 | Coronaviridae | 196 | 23 | 26 | 3 | 1.7 |
| 12 | Deltatvirus | 51 | 5 | 2 | 1 | 1.0 |
| 13 | Filoviridae | 54 | 13 | 10 | 3 | 1.3 |
| 14 | Flaviviridae | 503 | 82 | 65 | 13 | 4.2 |
| 15 | Hepadnaviridae | 901 | 15 | 11 | 10 | 5.3 |
| 16 | Herpesviridae | 80 | 47 | 43 | 168 | 22.0 |
| 17 | Iridoviridae | 13 | 16 | 12 | 2 | 1.3 |
| 18 | Orthomyxoviridae | 16480 | | 433+ | 28 | 6.6 |
| 19 | Papillomaviridae | 168 | 144 | 110 | 32 | 5.1 |
| 20 | Paramyxoviridae | 162 | 70 | 61 | 6 | 2.4 |
| 21 | Parvoviridae | 65 | 61 | 57 | 12 | 3.2 |
| 22 | Picornaviridae | 357 | 59 | 53 | 5 | 2.3 |
| 23 | Polyomaviridae | 454 | 28 | 26 | 5 | 2.1 |
| 24 | Poxviridae | 122 | 29 | 32 | 6 | 2.2 |
| 25 | Reoviridae | 852 | 736 | 695+ | 16 | 3.7 |
| 26 | Retroviridae | 1093 | 173 | 97 | 25 | 11.0 |
| 27 | Rhabdoviridae | 41 | 44 | 36 | 27 | 2.5 |
| 28 | Togaviridae | 96 | 31 | 26 | 8 | 3.0 |

[1]Primer sets of 10-15-mers have $45 \leq T_m \leq 50°$ C., hairpin $\Delta G \geq -3$ kcal/mol, primer dimer $\Delta G \geq -5$ kcal/mol, and generate amplicons of length 70-550 bp for all sequences (genomes or segments) in each family.
[2]Primer sets of 10-mers have $40 \leq T_m \leq 65°$ C., hairpin $\Delta G \geq -5$ kcal/mol, primer dimer $\Delta G \geq -7$ kcal/mol, and generate amplicons of length 60-600 bp for all sequences (genomes or segments) in each family.
[3]Maximum number of amplicons produced by the family's universal primer set for any genome from the indicated family, for 10-mer primer set.
[4]Mean number of amplicons produced by the family's universal primer set across genomes from the indicated family, for 10-mer primer set.

Following nucleic acid amplification, the lengths of the resulting amplicon fragments can be determined through separation using gradient electrophoresis. Individual fragments from a given species or strain of virus creates a unique electrophoretic banding signature. Examples of some fragment length distributions are given in Appendices B-D herein incorporated by reference in their entirety. The average number of electrophoretic bands per genome ranges from 1 to 22 across the viral families, while the maximum number of bands per genome ranges from 1 to 168 bands (see Table 8). For those families in which a large number of primers are required in the multiplexed universal set (e.g. Bunyaviridae, Orthomyxoviridae, and Reoviridae) or a large number of bands are produced for some genomes (e.g. Herpesviridae, Adenoviridae), the family may be subdivided to generate several smaller sets of primers, each of which will amplify fewer bands in a given genome. Another approach could be to use the primer set generated for all sequenced viruses taken together (not divided by family), breaking out various subgroups of primer pairs based on predicted multiplex compatibility. For example, multiplexed primers could be grouped so as to avoid undesired primer dimers and to have very similar $T_m$ values.

Figure 25:
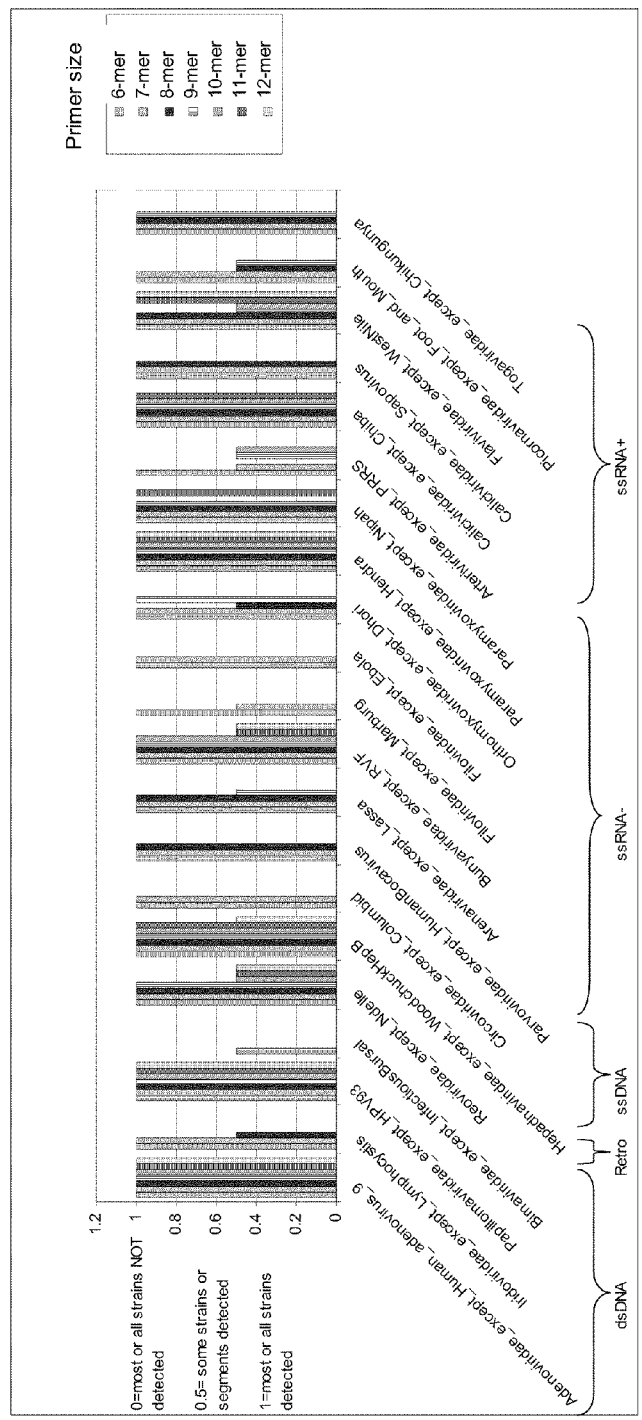
FIG. 25 shows a block diagram illustrating detection/identification of microorganisms using 6-mer to 11-mer primers.
Figure 26:
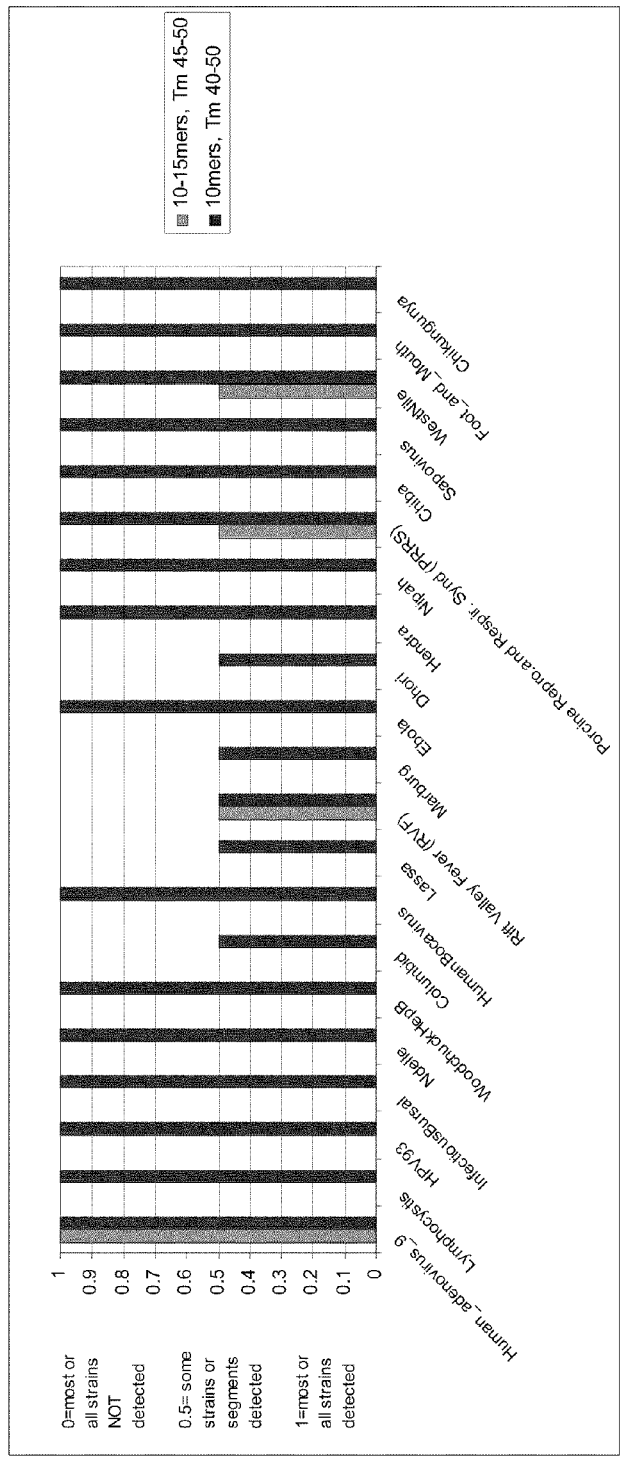
FIG. 26 shows a block diagram illustrating detection/identification of microorganisms using 10-15mers and 10mers primers.

Simulations were performed based on existing sequence data. The results are illustrated in FIGS. 25 and 26. In particular, those simulations indicate that discovery of unknown viruses by observation of new banding patterns in the primer set for the correct family of the previously unknown virus is unlikely for primers longer than 7 bases, since the probability of ≥8-mers being conserved among both known and uncharacterized viruses is less than that of 6-mers or 7-mers being conserved (FIG. 25).

The approach herein described, allows a methodology and application for generating genetic signatures for rapid, species/strain level identification of all viruses and microbes. Universal primer sets consisting of short (7-30 base pairs) nucleic acid strands have been created that can be used to amplify sequences of target viral DNA/RNA. These primer sets were designed to amplify specific nucleic acid sequences in the currently sequenced, vertebrate infecting viruses. Primer sets of the most highly conserved oligos for each family were built such that at least one amplicon would be generated from every full genome currently available in that family. This document describes the algorithm and software built to find such universal primer sets, as well as gives a few examples of universal primer sets that have been predicted. The actual primers generated will depend upon the input specifications desired (e.g. primer length, melting temperature range, amplicon length range, etc.). Amplified fragment length and/or sequence can be further examined using sequencing reactions or electrophoresis in order to characterize the organism. For example, simulations based on SARS as an example organism indicate that sequencing 4 or 5 randomly selected 100-mer fragments should provide very high confidence (>95%) of correctly classifying a novel virus to its correct family. Using the primers in a universal set would be very useful as sequencing primers. Accordingly, the simulations illustrated in FIG. 25 support the conclusions that detection/discovery of unknown viruses in their correct family is unlikely for anything longer than 7-mers.

However, discovery of previously unknown viruses is very likely using 10-mer (or shorter) primer sets from any family (at least one family) that is not necessarily the correct family for the unknown virus (FIG. 26). Using longer than 10-mer primers, e.g. isothermal 10-15-mer primer sets, drastically reduces the chances of discovering unknown viruses, either in the unknown virus' correct family or in any other family. The simulations shown in FIG. 26, indicate that it is not possible to detect all known viruses using 10-mers requiring primer Tm=45-50° C. The acceptable range must be widened to allow primer $T_m$'s as low as 40° C. if Applicants use 10-mers. With variable length, isothermal 10-15-mers with $T_m$=45-50° C., Applicants can detect all the known viruses, but most of the primers are longer than 10 bases. As a consequence, the simulations illustrated in FIG. 26, support the conclusions that detection/discovery of unknown viruses by primers in any family is likely for anything as long as 10-mers, but allowing longer primers drastically reduces the chance of discovery.

In some cases, instead of trying to selectively isolate and identify a given virus from a complex sample, every individual virus would be analyzed in parallel. By dealing with the sample in millions or billions of discrete sub-nanoliter volume reactors, every virus can, in parallel, be individually archived and analyzed. Primers and oligonucleotides determined by the proposed art would be added to the sample before it is divided. Because the microfluidic system is "digital", the sample could be divided into manageable subsets and analyzed using any combination of different oligomer and multiplex size. For example, for practical reasons related to the difficulty in reaction kinetics created by simultaneously amplifying a huge number of different targets, one might divide the sample into bins based on the viral family of interest or the thermodynamics of primer dimer avoidance. Each subsample would then only contain primers specific for a given viral family, limiting the complexity of the amplification reaction. There is also a trade off between using small oligomers, which are likely to hit on any sample (including unknowns), versus using larger oligomers with more specificity. Smaller-mers require a more limited multiplex, but also reduce the fragment resolution since for some viruses the primers in a set may amplify multiple bands, making it difficult to differentiate each fragment size in the distribution.

Software

All the steps of the methods herein described can be implemented as Perl® programs which call other underlying procedures or modules written in Perl® or other programs identifiable by a skilled person. The executable steps according to the methods and algorithms of the present disclosure can be stored on a medium, a computer or on a computer readable medium.

Hardware

All the software programs were developed, tested and installed on a single AMD Opteron 2.4 GHz processor or a Sun Solaris Processor. All programs should also be able to run with minimal modification on any computer that runs PERL.

The examples set forth above are provided to give those of ordinary skill in the art a complete disclosure and description of how to make and use the embodiments of the polynucleotides, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference in its entirety.

Further, each of the source code (a 93 kb txt file created on August 18 herein submitted as Appendix E) and the sequence listing (a 2,230 kb txt file created on Aug. 21, 2008) submitted herewith in computer readable form is incorporated herein by reference in its entirety.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Afonina, I., I. Ankoudinova, A. Mills, S. Lokhov, and P. Huynh. 2007. Primers with 5' flaps improve real-time PCR. BioTechniques 43:770-774.
2. Brownie, J., S. Shawcross, J. Theaker, D. Whitcombe, R. Ferrie, C. Newton, and S. Little. 1997. The elimination of primer-dimer accumulation in PCR. Nucleic Acids Research 25:3235-3241.
3. DeSantis, T., E. Brodie, J. Moberg, I. Zubieta, Y. Piceno, and G. Andersen. 2007. High-density universal 16S rRNA microarray analysis reveals broader diversity than typical clone library when sampling the environment. Microbial Ecology 53:371-383.
4. Ecker, D., J. Drader, J. Gutierrez, A. Gutierrez, J. Hannis, A. Schink, R. Sampath, and e. al. 2006. The Ibis T5000 universal biosensor: an automated platform for pathogen identification and strain typing. JALA 11:341-51.
5. Edwards, R. A., and F. Rohwer. 2005. Viral metagenomics. Nat Rev Micro 3:504-510.
6. Escutenaire, S., N. Mohamed, M. Isaksson, P. Thoren, B. Klingeborn, S. Belák, M. Berg, and J. Blomberg. 2007. SYBR Green real-time reverse transcription-polymerase chain reaction assay for the generic detection of coronaviruses. Archives of Virology 152:41-58.
7. Gardner, S. N., T. A. Kuczmarski, E. A. Vitalis, and T. R. Slezak. 2003. Limitations of TaqMan PCR for Detecting Divergent Viral Pathogens Illustrated by Hepatitis A, B, C, and E Viruses and Human Immunodeficiency Virus. J. Clin. Microbiol. 41:2417-2427.
8. Griffiths, D., P. Kellam, and R. Weiss. Jul. 6, 2002. Virus detection using degenerate PCR primers. International patent WO/2002/099130.
9. Kistler, A., P. Avila, S. Rouskin, D. Wang, T. Ward, S. Yagi, D. Schnurr, D. Ganem, J. DeRisi, and H. Boushey. 2007. Pan-viral screening of respiratory tract infections in adults with and without asthma reveals unexpected human coronavirus and human rhinovirus diversity. J Infect Dis 196:817-25.
10. Kistler, A., P. Avila, S. Rouskin, D. Wang, T. Ward, S. Yagi, D. Schnurr, D. Ganem, J. DeRisi, and H. Boushey. 2007. Pan-Viral Screening of Respiratory Tract Infections in Adults With and Without Asthma Reveals Unexpected Human Coronavirus and Human Rhinovirus Diversity. The Journal of Infectious Diseases 196:817-825.
11. Lamson, D., N. Renwick, V. Kapoor, Z. Liu, G. Palacios, J. Ju, A. Dean, K. St. George, T. Briese, and W. IanLipkin. 2006. MassTag Polymeraseâ€ Chainâ€ Reaction Detection of Respiratory Pathogens, Including a New Rhinovirus Genotype, That Caused Influenzaâ€ Like Illness in New York State during 2004â€'2005. The Journal of Infectious Diseases 194:1398-1402.
12. Lin, B., K. M. Blaney, A. P. Malanoski, A. G. Ligler, J. M. Schnur, D. Metzgar, K. L. Russell, and D. A. Stenger. 2007. Using a Resequencing Microarray as a Multiple Respiratory Pathogen Detection Assay. J. Clin. Microbiol. 45:443-452.
13. Lin, B., Z. Wang, G. J. Vora, J. A. Thornton, J. M. Schnur, D. C. Thach, K. M. Blaney, A. G. Ligler, A. P. Malanoski, J. Santiago, E. A. Walter, B. K. Agan, D. Metzgar, D. Seto, L. T. Daum, R. Kruzelock, R. K. Rowley, E. H. Hanson, C. Tibbetts, and D. A. Stenger. 2006. Broad-spectrum respiratory tract pathogen identification using resequencing DNA microarrays. Genome Res.: gr.4337206.
14. Mackenzie, J., K. Chua, P. Daniels, B. Eaton, H. Fields, R. Hal, K. Halpin, C. Johansen, P. Kirkland, S. Lam, P. McMinn, D. Nisbet, R. Paru, A. Pyke, S. Ritchie, P. Siba, D. Smith, G. Smith, A. van den Hurk, L. Wang, and D. Williams. 2001. Emerging viral diseases of Southeast Asia and the Western Pacific. Emerging Infectious Diseases 7, supplement: 497-504.
15. Margulies, M., M. Egholm, W. E. Altman, S. Attiya, J. S. Bader, L. A. Bemben, J. Berka, M. S. Braverman, Y.-J. Chen, Z. Chen, S. B. Dewell, L. Du, J. M. Fierro, X. V. Gomes, B. C. Godwin, W. He, S. Helgesen, C. H. Ho, G. P. Irzyk, S. C. Jando, M. L. I. Alenquer, T. P. Jarvie, K. B. Jirage, J.-B. Kim, J. R. Knight, J. R. Lanza, J. H. Leamon, S. M. Lefkowitz, M. Lei, J. Li, K. L. Lohman, H. Lu, V. B. Makhijani, K. E. McDade, M. P. McKenna, E. W. Myers, E. Nickerson, J. R. Nobile, R. Plant, B. P. Puc, M. T. Ronan, G. T. Roth, G. J. Sarkis, J. F. Simons, J. W. Simpson, M. Srinivasan, K. R. Tartaro, A. Tomasz, K. A. Vogt, G. A. Volkmer, S. H. Wang, Y. Wang, M. P. Weiner, P. Yu, R. F. Begley, and J. M. Rothberg. 2005. Genome sequencing in microfabricated high-density picoliter reactors. Nature 437:376-380.
16. Markham, N., and M. Zuker. 2005. DINAMelt web server for nucleic acid melting prediction. Nucleic Acids Research 33:W577-W581.
17. Nanda, S. 2007. Presented at the ASM Biodefense and Emerging Diseases Research Meeting, Washington, D.C.

18. Palacios, G., P. Quan, O. Jabado, S. Conlan, D. Hirschberg, Y. Liu, J. Zhai, N. Renwick, J. Hui, H. Hegyi, A. Grolla, J. Strong, J. Towner, T. Geisbert, P. Jahrling, C. Büchen-Osmond, H. Ellerbrok, M. Sanchez-Seco, Y. Lussier, P. Formenty, M. Nichol, H. Feldmann, T. Briese, and W. Lipkin. 2007. Panmicrobial oligonucleotide array for diagnosis of infectious diseases. Emerg Infect Dis. 13:73-81.
19. Pichon, J.-P., B. Bonnaud, and F. Mallet. 2007. Quantitative multiplex degenerate PCR for human endogenous retrovirus expression profiling. Nat. Protocols 1:2831-2838.
20. Png, A., K. Choo, C. Lee, S. Leong, and O. Kon. 2006. Primer design for whole genome amplification using genetic algorithms. In Silico Biology 6: 1-10.
21. Quan, P.-L., G. Palacios, O. J. Jabado, S. Conlan, D. L. Hirschberg, F. Pozo, P. J. M. Jack, D. Cisterna, N. Renwick, J. Hui, A. Drysdale, R. Amos-Ritchie, E. Baumeister, V. Savy, K. M. Lager, J. A. Richt, D. B. Boyle, A. Garcia-Sastre, I. Casas, P. Perez-Brena, T. Briese, and W. I. Lipkin. 2007. Detection of Respiratory Viruses and Subtype Identification of Influenza A Viruses by GreeneChipResp Oligonucleotide Microarray. J. Clin. Microbiol. 45:2359-2364.
22. Sampath, R., T. A. Hall, C. Massire, F. Li, L. B. Blyn, M. W. Eshoo, S. A. Hofstadler, and D. J. Ecker. 2007. Rapid Identification of Emerging Infectious Agents Using PCR and Electrospray Ionization Mass Spectrometry. Ann. N.Y. Acad. Sci. 1102:109-120.
23. Shuber, A., V. Grondin, and K. Klinger. 1995. A simplified procedure for developing multiplex PCRs. Genome Research 5:488-493.
24. Wang, D., L. Coscoy, M. Zylberberg, P. Avila, H. Boushey, D. Ganem, and J. DeRisi. 2002. Microarray-based detection and genotyping of viral pathogens. PNAS 99.
25. Wang, D., A. Urisman, Y. Liu, M. Springer, T. Ksiazek, and e. al. 2003. Viral Discovery and Sequence Recovery Using DNA Microarrays. PLoS Biology 1:e2 doi: 10.1371/journal.pbio.0000002.
26. Wang, X., L. Zhang, L. Jin, M. Jin, Z. Shen, S. An, F. Chao, and J. Ki. 2007. Development and application of an oligonucleotide microarray for the detection of food-borne bacterial pathogens. Applied Microbiology and Biotechnology 76:225-233.
27. Welzel, T. M., W. J. Miley, T. L. Parks, J. J. Goedert, D. Whitby, and B. A. Ortiz-Conde. 2006. Real-Time PCR Assay for Detection and Quantification of Hepatitis B Virus Genotypes A to G. J. Clin. Microbiol. 44:3325-3333.
28. Woolhouse, M. 2006. Where do emerging pathogens come from? Microbe 1:511-515.
29. Altschul, S. F., T. Madden, A. Schaffer, J. Zhang, Z. Zhang, W. Miller, and D. Lipman. 1997. Gapped BLAST and PSI-BLAST: a new generation of protein database search programs. Nucleic Acids Res. 25:3389-3402.
30. Casabianca, A., C. Gori, C. Orlandi, F. Forbici, C. Federico Perno, and M. Magnani. 2007. Fast and sensitive quantitative detection of HIV DNA in whole blood leucocytes by SYBR green I real-time PCR assay. Molecular and Cellular Probes 21:368-378.
31. Chenna, R., H. Sugawara, T. Koike, R. Lopez, T. J. Gibson, D. G. Higgins, and J. D. Thompson. 2003. Multiple sequence alignment with the Clustal series of programs. Nucl. Acids Res. 31:3497-3500.
32. Eddy, S. R. 1998. Profile hidden Markov models. Bioinformatics 14:755-763.
33. Edgar, R. C. 2004. MUSCLE: multiple sequence alignment with high accuracy and high throughput. Nucl. Acids Res. 32:1792-1797.
34. Gadberry, M. D., S. T. Malcomber, A. N. Doust, and E. A. Kellogg. 2005. Primaclade—a flexible tool to find conserved PCR primers across multiple species. Bioinformatics 21:1263-1264.
35. Huang, Y.-C., C.-F. Chang, C.-h. Chan, T.-J. Yeh, Y.-C. Chang, C.-C. Chen, and C.-Y. Kao. 2005. Integrated minimum-set primers and unique probe design algorithms for differential detection on symptom-related pathogens. Bioinformatics 21:4330-4337.
36. Jabado, O. J., G. Palacios, V. Kapoor, J. Hui, N. Renwick, J. Zhai, T. Briese, and W. I. Lipkin. 2006. Greene SCPrimer: a rapid comprehensive tool for designing degenerate primers from multiple sequence alignments. Nucl. Acids Res. 34:6605-6611.
37. Jarman, S. N. 2004. Amplicon: software for designing PCR primers on aligned DNA sequences. Bioinformatics 20:1644-1645.
38. Linhart, C., and R. Shamir. 2002. The degenerate primer design problem. Bioinformatics 18: S172-181.
39. Markham, N., and M. Zuker. 2005. DINAMelt web server for nucleic acid melting prediction. Nucleic Acids Research 33:W577-W581.
40. Rachlin, J., C. Ding, C. Cantor, and S. Kasif. 2005. MuPlex: multi-objective multiplex PCR assay design. Nucl. Acids Res. 33:W544-W547.
41. Rose, T., J. Henikoff, and S. Henikoff. 2003. CODEHOP (COnsensus-DEgenerate Hybrid Oligonucleotide Primer) PCR primer design. Nucl. Acids Res. 31:3763-3766.

Lengthy table referenced here

US09434997-20160906-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09434997B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09434997B2). An electronic copy of the "Sequence Listing" will also be available from the USPTO upon request and payment of the fee set forth in 37 CFR 1.19(b)(3).

What is claimed is:

1. A computer implemented method to identify a set of probe polynucleotides suitable for detecting a set of target microorganisms, the method comprising a processor:

receiving as input the set of target microorganisms;

receiving as input a set of rules to be satisfied by target sequences and related to hybridization of the target sequences to complementary polynucleotides;

identifying a set of target polynucleotides by selecting one or more target polynucleotides, each target polynucleotide comprised in at least one microorganism of the target microorganisms, each target polynucleotide comprising a target sequence satisfying to the set of rules; and identifying the set of probe polynucleotides by reverse complementing one or more of the target sequences of the target polynucleotides of the identified set of target polynucleotides, wherein identifying a set of target polynucleotides is performed by identifying a first target polynucleotide and a second target polynucleotide in at least one microorganism of the set of target microorganisms, wherein the second target polynucleotide comprises a target sequence satisfying to a rule requiring detection of said at least one microorganism performed by the second target polynucleotide in combination with the first target polynucleotide;

identifying one of the first and the second target polynucleotides in one or more additional target microorganisms, with the one or more additional target microorganisms different from the first target microorganism; and identifying one or more additional target polynucleotides in the one or more additional target microorganisms, wherein the one or more additional target polynucleotides comprise one or more additional target sequences satisfying to a rule requiring detection of said one or more additional target microorganisms performed by said one or more additional target polynucleotides in combination with the one of the first target polynucleotide and the second target polynucleotide, wherein the set of probe polynucleotides includes a first pair of probe polynucleotides identified by complementing target sequences of the first target polynucleotide or the second target polynucleotide and a second pair of probe polynucleotides identified by complementing target sequences of the one of the first target polynucleotide and the second target polynucleotide and target sequences of the one or more additional target polynucleotides;

wherein identifying a first target polynucleotide and a second target polynucleotide in at least one microorganism of the set of target microorganisms is performed by i) identifying a first set of candidate polynucleotides present in at least one of the target microorganisms;

ii) sorting the candidate polynucleotides of the first set by number of target microorganisms in which they occur;

iii) identifying second and third sets of candidate polynucleotides, said second and third sets comprising polynucleotides lying within a distance range of the polynucleotides of the first set of candidate polynucleotides, the second set comprising polynucleotides lying upstream of the first set, and the third set comprising polynucleotides lying downstream of the first set;

iv) sorting the candidate polynucleotides of the second and third sets by number of target microorganisms in which they occur;

v) selecting a most frequently occurring polynucleotide from the first set as the first target polynucleotide and a most frequently occurring polynucleotide from the second or third sets as the second target polynucleotide.

2. The method of claim 1, wherein the probe polynucleotides are primers, whereby a set of primers is being identified, the set of target polynucleotides comprises two or more target polynucleotides.

3. A computer implemented method to identify a set of probe polynucleotides suitable for detecting a set of target microorganisms, the method comprising a processor:

receiving as input the set of target microorganisms;

receiving as input a set of rules to be satisfied by target sequences and related to hybridization of the target sequences to complementary polynucleotides;

identifying a set of target polynucleotides by selecting one or more target polynucleotides, each target polynucleotide comprised in at least one microorganism of the target microorganisms, each target polynucleotide comprising a target sequence satisfying to the set of rules; and identifying the set of probe polynucleotides by reverse complementing one or more of the target sequences of the target polynucleotides of the identified set of target polynucleotides, wherein identifying a set of target polynucleotides is performed by identifying a first target polynucleotide and a second target polynucleotide in at least one microorganism of the set of target microorganisms, wherein the second target polynucleotide comprises a target sequence satisfying to a rule requiring detection of said at least one microorganism performed by the second target polynucleotide in combination with the first target polynucleotide;

identifying one of the first and the second target polynucleotides in one or more additional target microorganisms, with the one or more additional target microorganisms different from the first target microorganism; and identifying one or more additional target polynucleotides in the one or more additional target microorganisms, wherein the one or more additional target polynucleotides comprise one or more additional target sequences satisfying to a rule requiring detection of said one or more additional target microorganisms performed by said one or more additional target polynucleotides in combination with the one of the first target polynucleotide and the second target polynucleotide, wherein the set of probe polynucleotides includes a first pair of probe polynucleotides identified by complementing target sequences of the first target polynucleotide or the second target polynucleotide and a second pair of probe polynucleotides identified by complementing target sequences of the one of the first target polynucleotide and the second target polynucleotide and target sequences of the one or more additional target polynucleotides; and wherein identifying a first target polynucleotide and a second target polynucleotide in at least one microorganism of the set of target microorganisms is performed by
i) identifying a first set of candidate polynucleotides present in at least one of the target microorganisms;
ii) sorting the candidate polynucleotides of the first set by number of target microorganisms in which they occur;
iii) selecting a most frequently occurring polynucleotide as the first target polynucleotide;
iii) for all target microorganisms containing the first target polynucleotide, identifying a second set of candidate polynucleotides within an upstream or downstream distance range of the first target polynucleotide;
iv) sorting the candidate polynucleotides of the second set by number of target microorganisms in which they occur;
v) selecting a most frequently occurring polynucleotide from the sorted candidate polynucleotides of the second set as the second target polynucleotide.

4. A computer implemented method to identify a set of probe polynucleotides suitable for detecting a set of target microorganisms, the method comprising a processor:

receiving as input the set of target microorganisms;

receiving as input a set of rules to be satisfied by target sequences and related to hybridization of the target sequences to complementary polynucleotides;

identifying a set of target polynucleotides by selecting one or more target polynucleotides, each target polynucleotide comprised in at least one microorganism of the target microorganisms, each target polynucleotide comprising a target sequence satisfying to the set of rules; and identifying the set of probe polynucleotides by reverse complementing one or more of the target sequences of the target polynucleotides of the identified set of target polynucleotides, wherein identifying a set of target polynucleotides is performed by identifying a first target polynucleotide and a second target polynucleotide in at least one microorganism of the set of target microorganisms, wherein the second target polynucleotide comprises a target sequence satisfying to a rule requiring detection of said at least one microorganism performed by the second target polynucleotide in combination with the first target polynucleotide;

identifying one of the first and the second target polynucleotides in one or more additional target microorganisms, with the one or more additional target microorganisms different from the first target microorganism; and identifying one or more additional target polynucleotides in the one or more additional target microorganisms, wherein the one or more additional target polynucleotides comprise one or more additional target sequences satisfying to a rule requiring detection of said one or more additional target microorganisms performed by said one or more additional target polynucleotides in combination with the one of the first target polynucleotide and the second target polynucleotide, wherein the set of probe polynucleotides includes a first pair of probe polynucleotides identified by complementing target sequences of the first target polynucleotide or the second target polynucleotide and a second pair of probe polynucleotides identified by complementing target sequences of the one of the first target polynucleotide and the second target polynucleotide and target sequences of the one or more additional target polynucleotides; and wherein identifying a first target polynucleotide and a second target polynucleotide in at least one microorganism of the set of target microorganisms is performed by
i) identifying a set of candidate polynucleotides present in at least one of the target microorganisms;
ii) sorting pairs of the candidate polynucleotides of the set by number of target microorganisms in which they occur within a predetermined distance from each other;
iii) selecting the most frequently occurring pair as the first target polynucleotide and the second polynucleotide respectively.

5. A computer implemented method to select a set of probe polynucleotides configured for detecting a set of target microorganisms, the method comprising a processor:

defining features of target polynucleotides according to a set of rules for sequences of the target polynucleotides;

selecting one or more target polynucleotides of the target polynucleotides by:
i) selecting from the target polynucleotides a first set of candidate polynucleotides present in at least one of the target microorganisms;
ii) sorting the candidate polynucleotides of the first set by number of target microorganisms in which they occur;
iii) selecting a second and third sets of candidate polynucleotides, said second and third sets comprising polynucleotides lying in the at least one of the target microorganism within a distance range of a most frequently occurring polynucleotide of the polynucleotides of the first set of candidate polynucleotides, the second set comprising polynucleotides lying upstream of the most frequently occurring polynucleotide of the first set, and the third set comprising polynucleotides lying downstream of the most frequently occurring polynucleotide of the first set;

iv) sorting the candidate polynucleotides of the second and third sets by number of target microorganisms in which they occur; and v) selecting the most frequently occurring polynucleotide from the first set as a first target polynucleotide and a most frequently occurring polynucleotide from the second or third sets as a second target polynucleotide;

reverse complementing one of the first and second target polynucleotides to obtain a set of probe polynucleotides configured to detect at least one microorganism of the target microorganisms.

6. The method of claim 5, wherein the detection is performed for identification, tracking, or monitoring of infectious diseases.

7. The method of claim 5, wherein the target microorganisms are identified or unidentified pathogens.

8. The method of claim 5, wherein the target microorganisms comprise influenza A, HIV1, Ebola, Norwalk virus, avian influenza, SARS coronavirus, Nipah virus, Hendra virus, Australian bat lyssavirus, Crimean Congo hemorrhagic fever, Venezuelan equine encephalitis, West Nile virus, Hanta virus, hepatitis C, Marburg virus, and foot and mouth disease virus.

9. A computer implemented method to select a set of probe polynucleotides configured to selectively amplify a set of target polynucleotide fragments through PCR amplification prior to sequencing, the method comprising a processor:

defining features of probe polynucleotides according to a set of rules for sequences of the probe polynucleotides;

selecting one or more probe polynucleotides of the probe polynucleotides by:

i) selecting from the probe polynucleotides a first set of candidate probe polynucleotides present in at least one of the target polynucleotide fragments;

ii) sorting the candidate probe polynucleotides of the first set by number of target polynucleotide fragments in which they occur;

iii) selecting a second and third set of candidate probe polynucleotides, said second and third sets comprising polynucleotides lying in the at least one of the target fragments within a distance range of a most frequently occurring polynucleotide of the polynucleotides of the first set of candidate probe polynucleotides, the second set comprising polynucleotides lying upstream of the most frequently occurring polynucleotide of the first set, and the third set comprising polynucleotides lying downstream of the most frequently occurring polynucleotide of the first set;

wherein the distance range satisfies a rule requiring amplification of said at least one target polynucleotide fragment performed by the second or the third target probe polynucleotide in combination with the first target probe polynucleotide;

iv) sorting the candidate probe polynucleotides of the second and third sets by number of target polynucleotide fragments in which they occur; and v) selecting the most frequently occurring probe polynucleotide from the first set as a first target probe polynucleotide and a most frequently occurring polynucleotide from the second or third sets as a second target probe polynucleotide;

vi) reverse complementing one of the first and second target probe polynucleotides to obtain a set of probe polynucleotides configured to detect at least one target polynucleotide fragment of the target polynucleotide fragments in a sample;

vii) updating a list of target polynucleotide fragments to be amplified by eliminating from the list target polynucleotide fragments having desired number of valid amplicons generated by any combination of probes in the set of selected probes; and viii) repeating steps ii) through vi) until desired number of detectable amplicons has been generated for all target polynucleotide fragments to be amplified.

10. A computer implemented method to select a set of probe polynucleotides configured for use in an array for hybridizing target polynucleotide fragments, the method comprising a processor:

defining features of target probe polynucleotides according to a set of rules for sequences of the target probe polynucleotides, wherein the set of rules comprises lengths of the target probe polynucleotides and other parameters that determine the target probe polynucleotide's capability to hybridize to a target polynucleotide fragment to form a probe polynucleotide-target polynucleotide complex;

selecting one or more probe polynucleotides of the probe polynucleotides by:

i) selecting from the target probe polynucleotides a first set of candidate polynucleotides present in at least one of the target polynucleotide fragments;

ii) sorting the candidate polynucleotides of the first set by number of target polynucleotide fragments in which they occur;

iii) excluding from the first set of target probe polynucleotides, polynucleotides configured to hybridize other probe polynucleotides of the first set to form probe polynucleotide-probe polynucleotide complexes, or with non-target polynucleotide fragments to form probe polynucleotide-non-target polynucleotide complexes;

iv) selecting the most frequently occurring polynucleotide from the first set as a first target probe polynucleotide;

v) repeating steps ii) through iv) until each target polynucleotide fragment has desired number of probe polynucleotides capable of hybridizing it.

* * * * *

UNITED STATES PATENT AND TRADEMARK OFFICE
CERTIFICATE OF CORRECTION

PATENT NO. : 9,434,997 B2
APPLICATION NO. : 12/196238
DATED : September 6, 2016
INVENTOR(S) : Bill W. Colston, Jr. et al.

Page 1 of 1

It is certified that error appears in the above-identified patent and that said Letters Patent is hereby corrected as shown below:

In the Specification

Under the title "STATEMENT OF GOVERNMENT GRANT", Column 1, Lines 16-20, delete the paragraph "The United States Government has rights in this invention pursuant to Contract No. DE-AC52-07NA27344 between the U.S. Department of Energy and Lawrence Livermore National Security, LLC, for the operation of Lawrence Livermore National Security."

And replace with the paragraph "The United States Government has rights in this invention pursuant to Contract No. DE-AC52-07NA27344 between the United States Department of Energy and Lawrence Livermore National Security, LLC, for the operation of Lawrence Livermore National Laboratory."

Signed and Sealed this
Fourteenth Day of May, 2019

Andrei Iancu
*Director of the United States Patent and Trademark Office*